US011072799B2

(12) United States Patent
Gill et al.

(10) Patent No.: US 11,072,799 B2
(45) Date of Patent: Jul. 27, 2021

(54) GENE ENCODING FHB1 RESISTANCE TO FUSARIUM HEAD BLIGHT DISEASE AND USES THEREOF

(71) Applicants: Kansas State University Research Foundation, Manhattan, KS (US); Regents of The University Of Minnesota, Minneapolis, MN (US)

(72) Inventors: Bikram Gill, Manhattan, KS (US); Nidhi Rawat, Greenbelt, MD (US); Eduard Akhunov, Manhattan, KS (US); Michael Pumphrey, Pullman, WA (US); James A. Anderson, Woodbury, MN (US); Sixin Liu, Purcellville, VA (US)

(73) Assignees: Kansas State University Research Foundation, Manhattan, KS (US); Regents of The University Of Minnesota, Minneapolis, MN (US)

( * ) Notice: Subject to any disclaimer, the term of this patent is extended or adjusted under 35 U.S.C. 154(b) by 142 days.

(21) Appl. No.: 16/504,535

(22) Filed: Jul. 8, 2019

(65) Prior Publication Data

US 2019/0323026 A1 Oct. 24, 2019

Related U.S. Application Data

(63) Continuation of application No. 15/315,139, filed as application No. PCT/US2015/033290 on May 29, 2015, now Pat. No. 10,344,297.

(60) Provisional application No. 62/005,079, filed on May 30, 2014.

(51) Int. Cl.
*C12N 15/82* (2006.01)
*C07K 14/415* (2006.01)

(52) U.S. Cl.
CPC ........ *C12N 15/8282* (2013.01); *C07K 14/415* (2013.01)

(58) Field of Classification Search
CPC .......................... C12N 15/8282; C07K 14/415
See application file for complete search history.

(56) References Cited

U.S. PATENT DOCUMENTS

| | | | | |
|---|---|---|---|---|
| 6,197,518 | B1 * | 3/2001 | Procunier | C12Q 1/6895 435/6.12 |
| 2007/0044171 | A1 | 2/2007 | Kovalic et al. | |
| 2011/0167514 | A1 | 7/2011 | Brover et al. | |
| 2012/0222172 | A1 | 8/2012 | Ohm | |

OTHER PUBLICATIONS

Bernardo, Amy N., et al. "Single nucleotide polymorphism in wheat chromosome region harboring Fhb1 for Fusarium head blight resistance." Molecular breeding 29.2 (2012): 477-488. (Year: 2012).*

International Search Report and Written Opinion dated Nov. 23, 2015, in the PCT/US15/33290 filed May 29, 2015.

Gunnauah, Raghavendra "Intergrated Matabolo-Proteomic Approach to Decipher the Mechanisms by Which Wheat QTL (Fhb1) Contributes to Resistance against Fusarium graminearum," PLoS One, Jul. 2012, vol. 7 (7).

TSA: Triticum aestivum cultivar Wangshuibai, transcriptome shotgun assembly.

Xiao, Jin, "Transcriptome-based discovery of pathways and genes related to resistance against Fusarium head blight in wheat landrace Wangshuibai," BMC Genomics 2013, vol. 14 (197).

Office Action in corresponding U.S. Appl. No. 15/315,139, dated Feb. 22, 2018.

Office Action in corresponding U.S. Appl. No. 15/315,139, dated Jul. 26, 2018.

* cited by examiner

*Primary Examiner* — Weihua Fan
(74) *Attorney, Agent, or Firm* — Hovey Williams LLP

(57) ABSTRACT

Methods and recombinant vectors for increasing resistance to *Fusarium* head blight (FHB) infection in plants. Exogenous Fhb1 nucleic acids are described to generate transgenic plants having increased resistance to FHB relative to a control plant. The nucleotide sequence of the exogenous nucleic acid comprises SEQ ID NO:1, 2, 4, 5, or 6; has at least 95% sequence identity to SEQ ID NO:1, 2, 4, 5, or 6; encodes a protein comprising the amino acid sequence of SEQ ID NO: 3, 7, 8, or 9; or encodes a protein having at least 95% amino acid identity to SEQ ID NO: 3, 7, 8, or 9.

19 Claims, 4 Drawing Sheets

Specification includes a Sequence Listing.

```
R-NIL      TTTCACCAATAAAGATGGAGTTGTCCGTATAAAATCCAACTATTTCGACATGTTTTGGAG 2520
MUT-1958   TTTCACCAATAAAGATGGAGTTGTCCGTATAAAATCCAACTATTTCGACATGTTTTGGAG 2520
MUT-1284   TTTCACCAATAAAGATGGAGTTGTCCGTATAAAATCCAACTATTTCGACATGTTTTGAAG 2520
           ********************************************************* **

R-NIL      GCGAAGCCCAAATTGGATCTGGGCTGATTCAACTGACACCACCCACAACAACCGTGATAC 2580
MUT-1958   GCGAAGCCCAAATTGGATCTGGGCTGATTCAACTGACACCACCCACAACAACCGTGATAC 2580
MUT-1284   GCGAAGCCCAAATTGGATCTGGGCTGATTCAACTGACACCACCCACAACAACCGTGATAC 2580
           ************************************************************

R-NIL      ATTATTCAAGGTGACCACTGGGCCCGACTTCATTGCTCTGCGAAACTTGGGCAACAACAA 2640
MUT-1958   ATTATTCAAGGTGACCACTGGGCCCGACTTCATTGCTCTGCGAAACTTGGGCAACAACAA 2640
MUT-1284   ATTATTCAAGGTGACCACTGGGCCCGACTTCATTGCTCTGCGAAACTTGGGCAACAACAA 2640
           ************************************************************

R-NIL      TTTCTGCAAAAGGTTAACCACAGAAGGGAAGTATGATTGCCTCAATGCTGCTGTTGGTTC 2700
MUT-1958   TTTCTGCAAAAGGTTAACCACAGAAGGGAAGTATGATTGCCTCAATGCTGCTGTTGGTTC 2700
MUT-1284   TTTCTGCAAAAGGTTAACCACAGAAGGGAAGTATGATTGCCTCAATGCTGCTGTTGGTTC 2700
           ************************************************************

R-NIL      CATCACAGCTGAAGTAAAAATGCGGTGCATTGAACCAATTGTTTCTCGAGACATCTATGA 2760
MUT-1958   CATCACAGCTGAAGTAAAAATGCGGTGCATTGAACCAATTGTTTCTCGAGACATCTATGA 2760
MUT-1284   CATCACAGCTGAAGTAAAAATGCGGTGCATTGAACCAATTGTTTCTCGAGACATCTATGA 2760
           ************************************************************

R-NIL      TGTTGATTTTCGCCTAGGTGAAGCTAAGATCTACACCAATGGTATTGAGGGCCTTGATAG 2820
MUT-1958   TGTTGATTTTCGCCTAGGTGAAGCTAAGATCTACACCAATGGTATTGAGGGCCTTGATAG 2820
MUT-1284   TGTTGATTTTCGCCTAGGTGAAGCTAAGATCTACACCAATGGTATTGAGGGCCTTGATAG 2820
           ************************************************************

R-NIL      TCAAATTGTTGAAAACATGACCACCACAACAAACAAAACCAAAATGATCTTCACATACAC 2880
MUT-1958   TCAAATTGTTGAAAACATGACCACCACAACAAACAAAACCAAAATGATCTTCACATACAC 2880
MUT-1284   TCAAATTGTTGAAAACATGACCACCACAACAAACAAAACCAAAATGATCTTCACATACAC 2880
           ************************************************************

R-NIL      AAATACCGTCCAGAGTACCTGGAGTTCTACTGTTTCATTGAAGATTGGCGTCAAGACCAA 2940 (SEQ ID NO: 22)
MUT-1958   AAATACCGTCCAGAGTACCTAGAGTTCTACTGTTTCATTGAAGATTGGCGTCAAGACCAA 2940 (SEQ ID NO: 23)
MUT-1284   AAATACCGTCCAGAGTACCTGGAGTTCTACTGTTTCATTGAAGATTGGCGTCAAGACCAA 2940 (SEQ ID NO: 24)
           ******************** ***************************************
```

Figure 3

```
R-NIL      DGLVHVRCCYNNKYWAPQQRLLHGSARWTIGTANELEEDLSKPSCTLFKHIPVSGEDGST 120
MUT-1958   DGLVHVRCCYNNKYWAPQQRLLHGSARWTIGTANELEEDLSKPSCTLFKHIPVSGEDGST 120
MUT-1284   DGLVHVRCCYNNKYWAPQQRLLHGSARWTIGTANELEEDLSKPSCTLFKHIPVSGEDGST 120
           ************************************************************

R-NIL      CRFLHSQLGKYACVLSSSDMSKHPYLHIAREESDQDNLLDAFTVLDVSEQMQLPSYLAFK 180
MUT-1958   CRFLHSQLGKYACVLSSSDMSKHPYLHIAREESDQDNLLDAFTVLDVSEQMQLPSYLAFK 180
MUT-1284   CRFLHSQLGKYACVLSSSDMSKHPYLHIAREESDQDNLLDAFTVLDVSEQMQLPSYLAFK 180
           ************************************************************

R-NIL      GDNGRFLGAKIVEGYRYLEYSKDDIGDLSVLHTIFTNKDGVVRIKSNYFDMFWRRSPNWI 240
MUT-1958   GDNGRFLGAKIVEGYRYLEYSKDDIGDLSVLHTIFTNKDGVVRIKSNYFDMFWRRSPNWI 240
MUT-1284   GDNGRFLGAKIVEGYRYLEYSKDDIGDLSVLHTIFTNKDGVVRIKSNYFDMF -------- 232
           ****************************************************

R-NIL      WADSTDTTHNNRDTLFKVTTGPDFIALRNLGNNNFCKRLTTEGKYDCLNAAVGSITAEVK 300
MUT-1958   WADSTDTTHNNRDTLFKVTTGPDFIALRNLGNNNFCKRLTTEGKYDCLNAAVGSITAEVK 300
MUT-1284   ------------------------------------------------------------ 232

R-NIL      MRCIEPIVSRDIYDVDFRLGEAKIYTNGIEGLDSQIVENMTTTTNKTKMIFTYTNTVQST 360
MUT-1958   MRCIEPIVSRDIYDVDFRLGEAKIYTNGIEGLDSQIVENMTTTTNKTKMIFTYTNTVQST 360
MUT-1284   ------------------------------------------------------------ 232

R-NIL      WSSTVSLKIGVKTKFKSGIPFVVDGEVEVSTEFSGSYTWGGAKSDTKVVSKQIDVEVPPM 420
MUT-1958    ----------------------------------------------------------- 360
MUT-1284   ------------------------------------------------------------ 232

R-NIL      KKVTVKAIGSNGLCDIPFSYKQRDILTNGDEVIQEFTDGMYFGVKTSSITFHTKEEHL   478 (SEQ ID NO: 25)
MUT-1958   ----------------------------------------------------------   360 (SEQ ID NO: 26)
MUT-1284   ----------------------------------------------------------   232 (SEQ ID NO: 27)
```

Figure 4

SEQUENCE LISTING

<160> NUMBER OF SEQ ID NOS: 27

<210> SEQ ID NO 1
<211> LENGTH: 3472
<212> TYPE: DNA
<213> ORGANISM: Triticum aestivum

<400> SEQUENCE: 1

```
acggccctga acactgagca gtgtgtagta acacaaaata taggaaaaaa atgtttccgc     60
tgtcagcttt gccgagatgc gtcgctctcc gctcaaagca tggcaacagc tacctgcgct    120
ccgtgcacga caagagccag ggcggcaact tcgtcgagct aagcgccgac aacgacggag    180
gcgtcatgaa cccacgctgc agattctacc tggaggcgtc caaggagcac gacgggctcg    240
ttcacgtcag atgttgctac aacaacaagt actgggcgcc gcagcagcgc ctgcttcacg    300
gcagcgctcg ctggaccatt ggtaccgcaa atgagctgga ggaggatctc tccaagccat    360
catgcaccct gtttaagcac atccccgtct cgggcgagga cggctccacc tgcaggttcg    420
tttactgctg taaataattt aagcacgtcc ctctttccac ctctctcgct gctcctgaat    480
ccagacaggc ctccttaccc cccttctctc tcttttcctc gggtgggccg agagatgtgg    540
aagggaggcc cagactaaaa gtaatcgatt tattgggatg catggttcga cgttgaggtc    600
ggtctggatt tattgtattt ggttataaat aaactaaaaa ataaacaatt gggaagaaac    660
acgaatgagc aataaactaa aaataaattt attgtatttg gttataaaat aattcttgaa    720
tcgaaagttt tttccgaggc atggttgcac ttgcacgttg aggtcgccct tttctatgc     780
atgcttgcat gttgatgtga catgtttgca tgttgaaaaa tttcttaatg ggatcagtta    840
tttagttcgt ataggattaa tagggatcat gcagatttta tgtatccact gtgatgtact    900
agtgttagag caactctatc aacatcgtca atctaccctg tcgccattat aaccgtttga    960
caaaatgata gtctagcaga gtcgccatct tgtcggggat catcataatt tatgaagcac   1020
cctccatatc tggcctctca ggcgccatat atagcgcctc ggggttgcgt tttagataca   1080
tagcccacgt ggttgatact tactctagta tacaaaggag atgatatgat gtccatttag   1140
tatgtaagct tgacattcac aagattatct aaaaattata aaactattct tttgatcttt   1200
tgaactgtta atctaatgta cactcatttt cacagtttac ttaattactt accttgtaca   1260
agtactgcaa acgaaatgtt gtgttcttat tggtcatgac tccaagaaga cgtcttctag   1320
gctcattgga attcttctaa ctagatgtta ccctgtgtgt tgctgcgaca aatgtttgca   1380
gcatatttca gtgggatttg attatatgaa catgatattt gcatgaataa taaggactaa   1440
aagcccaata atccatttct aaacccaggc tcatctgcac ccgcgttgac gaaaaaaatc   1500
aaaacaaata ctataaaaat taaaaaaaaa atcaactttt tttgtgtggt agataatttg   1560
gagccgtgag gttcgctcct attttcaaat catttggaca tttgtgccgc tctcggaaaa   1620
aaagacaaat ccgggttctg taaaaaaagt ttactgttca cgcacttttt gacccgattt   1680
gtcttttttg ctgagagtta ctcagatgtc taaatgattt gaaaattaga gcgaaccaca   1740
agcatcaaat tatctaccac acaaaataat tttgattttt ttctagtatt tgttttgaat   1800
tttttcctaa ccgagtgagg atgagcctgt gcaccggaaa cgccgcaccc ctaaaaccca   1860
aaatacatat gcttaatgca taattataaa atatatattg attatcacta tggtaatata   1920
tttataaagt tcgaaccttt ttgtgtgcat agttatatct tgatgtttgt cttttcccat   1980
gcatggttgt atgttgaggc ggcattattg atgttgaggt aaatatgtta gtgggatcac   2040
ctacttagct atatatggca cacgctacat tgcttaaata aatagtctca tattttggtg   2100
```

-continued tatgtcaacc agcagggata cagcctgact ttcgtgatta tctctcccat cttatgtttg 2160
caatcgtttg tttgtacatg gcaggttcct tcattcccag ctaggaaaat atgcttgcgt 2220
gctatccagt tctgatatgt ccaagcaccc ctacttgcat atagcacgtg aagaatctga 2280
tcaagataat ctccttgatg cttttactgt ccttgatgtg tcagaacaga tgcagttgcc 2340
tagttatctt gctttcaaag gcgacaatgg gaggttcctt ggtgcgaaga tcgtcgaggg 2400
ttatagatat cttgaatact ccaaagatga tattggagat ctaagtgtgt tgcacacaat 2460
tttcaccaat aaagatggag ttgtccgtat aaaatccaac tatttcgaca tgttttggag 2520
gcgaagccca aattggatct gggctgattc aactgacacc acccacaaca accgtgatac 2580
attattcaag gtgaccactg ggcccgactt cattgctctg cgaaacttgg gcaacaacaa 2640
tttctgcaaa aggttaacca cagaagggaa gtatgattgc ctcaatgctg ctgttggttc 2700
catcacagct gaagtaaaaa tgcggtgcat tgaaccaatt gtttctcgag acatctatga 2760
tgttgatttt cgcctaggtg aagctaagat ctacaccaat ggtattgagg gccttgatag 2820
tcaaattgtt gaaaacatga ccaccacaac aaacaaaacc aaaatgatct tcacatacac 2880
aaataccgtc cagagtacct ggagttctac tgtttcattg aagattggcg tcaagaccaa 2940
atttaaatcc gggattccat ttgtagttga cggcgaagtt gaggtcagca ctgagtttag 3000
tggatcatat acctgggggg gagccaaatc tgacacaaaa gtagtaagca aacaaattga 3060
tgttgaagtt cctccaatga agaaagtgac agtaaaagcg attggatcaa acggtttatg 3120
tgatatacct ttctcataca agcagaggga tattctaacc aatggagatg aagttatcca 3180
agaattcacc gatggcatgt attttggtgt taaaacctcc agcatcacgt tccataccaa 3240
agaagaacac ctgtgaggag gactgaagag gtgtgcatgg gtcgtgagag gtgaaaccta 3300
catcagatgt gctacctaaa taaagatgta gtgaacatgc gtatatgaat gggtcgtggc 3360
ttgttttcga tggagctggt ttgagtgctt tctttccttc ctatgtgttg ggaataaaat 3420
ctaagtttag gatgtatttg gtttgacgaa atcaatatta taattattat ca 3472

<210> SEQ ID NO 2
<211> LENGTH: 1437
<212> TYPE: DNA
<213> ORGANISM: Triticum aestivum

<400> SEQUENCE: 2
atgtttccgc tgtcagcttt gccgagatgc gtcgctctcc gctcaaagca tggcaacagc 60
tacctgcgct ccgtgcacga caagagccag ggcggcaact tcgtcgagct aagcgccgac 120
aacgacggag gcgtcatgaa cccacgctgc agattctacc tggaggcgtc caaggagcac 180
gacgggctcg ttcacgtcag atgttgctac aacaacaagt actgggcgcc gcagcagcgc 240
ctgcttcacg gcagcgctcg ctggaccatt ggtaccgcaa atgagctgga ggaggatctc 300
tccaagccat catgcaccct gtttaagcac atccccgtct cgggcgagga cggctccacc 360
tgcaggttcc ttcattccca gctaggaaaa tatgcttgcg tgctatccag ttctgatatg 420
tccaagcacc cctacttgca tatagcacgt gaagaatctg atcaagataa tctccttgat 480
gcttttactg tccttgatgt gtcagaacag atgcagttgc ctagttatct tgctttcaaa 540
ggcgacaatg ggaggttcct tggtgcgaag atcgtcgagg gttatagata tcttgaatac 600
tccaaagatg atattggaga tctaagtgtg ttgcacacaa ttttcaccaa taaagatgga 660
gttgtccgta taaaatccaa ctatttcgac atgttttgga ggcgaagccc aaattggatc 720

-continued

```
tgggctgatt caactgacac cacccacaac aaccgtgata cattattcaa ggtgaccact    780

gggcccgact tcattgctct gcgaaacttg ggcaacaaca atttctgcaa aaggttaacc    840

acagaaggga agtatgattg cctcaatgct gctgttggtt ccatcacagc tgaagtaaaa    900

atgcggtgca ttgaaccaat tgtttctcga gacatctatg atgttgattt tcgcctaggt    960

gaagctaaga tctacaccaa tggtattgag ggccttgata gtcaaattgt tgaaaacatg   1020

accaccacaa caaacaaaac caaaatgatc ttcacataca caaataccgt ccagagtacc   1080

tggagttcta ctgtttcatt gaagattggc gtcaagacca aatttaaatc cgggattcca   1140

tttgtagttg acggcgaagt tgaggtcagc actgagttta gtggatcata tacctggggg   1200

ggagccaaat ctgacacaaa agtagtaagc aaacaaattg atgttgaagt tcctccaatg   1260

aagaaagtga cagtaaaagc gattggatca aacggtttat gtgatatacc tttctcatac   1320

aagcagaggg atattctaac caatggagat gaagttatcc aagaattcac cgatggcatg   1380

tattttggtg ttaaaacctc cagcatcacg ttccatacca aagaagaaca cctgtga      1437
```

<210> SEQ ID NO 3
<211> LENGTH: 478
<212> TYPE: PRT
<213> ORGANISM: Triticum aestivum

<400> SEQUENCE: 3

```
Met Phe Pro Leu Ser Ala Leu Pro Arg Cys Val Ala Leu Arg Ser Lys
1               5                   10                  15

His Gly Asn Ser Tyr Leu Arg Ser Val His Asp Lys Ser Gln Gly Gly
            20                  25                  30

Asn Phe Val Glu Leu Ser Ala Asp Asn Asp Gly Gly Val Met Asn Pro
        35                  40                  45

Arg Cys Arg Phe Tyr Leu Glu Ala Ser Lys Glu His Asp Gly Leu Val
    50                  55                  60

His Val Arg Cys Cys Tyr Asn Asn Lys Tyr Trp Ala Pro Gln Gln Arg
65                  70                  75                  80

Leu Leu His Gly Ser Ala Arg Trp Thr Ile Gly Thr Ala Asn Glu Leu
                85                  90                  95

Glu Glu Asp Leu Ser Lys Pro Ser Cys Thr Leu Phe Lys His Ile Pro
            100                 105                 110

Val Ser Gly Glu Asp Gly Ser Thr Cys Arg Phe Leu His Ser Gln Leu
        115                 120                 125

Gly Lys Tyr Ala Cys Val Leu Ser Ser Ser Asp Met Ser Lys His Pro
    130                 135                 140

Tyr Leu His Ile Ala Arg Glu Glu Ser Asp Gln Asp Asn Leu Leu Asp
145                 150                 155                 160

Ala Phe Thr Val Leu Asp Val Ser Glu Gln Met Gln Leu Pro Ser Tyr
                165                 170                 175

Leu Ala Phe Lys Gly Asp Asn Gly Arg Phe Leu Gly Ala Lys Ile Val
            180                 185                 190

Glu Gly Tyr Arg Tyr Leu Glu Tyr Ser Lys Asp Asp Ile Gly Asp Leu
        195                 200                 205

Ser Val Leu His Thr Ile Phe Thr Asn Lys Asp Gly Val Val Arg Ile
    210                 215                 220

Lys Ser Asn Tyr Phe Asp Met Phe Trp Arg Arg Ser Pro Asn Trp Ile
225                 230                 235                 240

Trp Ala Asp Ser Thr Asp Thr Thr His Asn Asn Arg Asp Thr Leu Phe
                245                 250                 255
```

-continued

```
Lys Val Thr Thr Gly Pro Asp Phe Ile Ala Leu Arg Asn Leu Gly Asn
            260                 265                 270

Asn Asn Phe Cys Lys Arg Leu Thr Thr Glu Gly Lys Tyr Asp Cys Leu
        275                 280                 285

Asn Ala Ala Val Gly Ser Ile Thr Ala Glu Val Lys Met Arg Cys Ile
    290                 295                 300

Glu Pro Ile Val Ser Arg Asp Ile Tyr Asp Val Asp Phe Arg Leu Gly
305                 310                 315                 320

Glu Ala Lys Ile Tyr Thr Asn Gly Ile Glu Gly Leu Asp Ser Gln Ile
                325                 330                 335

Val Glu Asn Met Thr Thr Thr Thr Asn Lys Thr Lys Met Ile Phe Thr
            340                 345                 350

Tyr Thr Asn Thr Val Gln Ser Thr Trp Ser Ser Thr Val Ser Leu Lys
        355                 360                 365

Ile Gly Val Lys Thr Lys Phe Lys Ser Gly Ile Pro Phe Val Val Asp
    370                 375                 380

Gly Glu Val Glu Val Ser Thr Glu Phe Ser Gly Ser Tyr Thr Trp Gly
385                 390                 395                 400

Gly Ala Lys Ser Asp Thr Lys Val Val Ser Lys Gln Ile Asp Val Glu
                405                 410                 415

Val Pro Pro Met Lys Lys Val Thr Val Lys Ala Ile Gly Ser Asn Gly
            420                 425                 430

Leu Cys Asp Ile Pro Phe Ser Tyr Lys Gln Arg Asp Ile Leu Thr Asn
        435                 440                 445

Gly Asp Glu Val Ile Gln Glu Phe Thr Asp Gly Met Tyr Phe Gly Val
    450                 455                 460

Lys Thr Ser Ser Ile Thr Phe His Thr Lys Glu Glu His Leu
465                 470                 475


<210> SEQ ID NO 4
<211> LENGTH: 480
<212> TYPE: DNA
<213> ORGANISM: Triticum aestivum

<400> SEQUENCE: 4

ttgccgagat gcgtcgctct ccgctcaaag catggcaaca gctacctgcg ctccgtgcac      60

gacaagagcc agggcggcaa cttcgtcgag ctaagcgccg acaacgacgg aggcgtcatg     120

aacccacgct gcagattcta cctggaggcg tccaaggagc acgacgggct cgttcacgtc     180

agatgttgct acaacaacaa gtactgggcg ccgcagcagc gcctgcttca cggcagcgct     240

cgctggacca ttggtaccgc aaatgagctg gaggaggatc tctccaagcc atcatgcacc     300

ctgtttaagc acatccccgt ctcgggcgag gacggctcca cctgcaggtt ccttcattcc     360

cagctaggaa aatatgcttg cgtgctatcc agttctgata tgtccaagca cccctacttg     420

catatagcac gtgaagaatc tgatcaagat aatctccttg atgcttttac tgtccttgat     480


<210> SEQ ID NO 5
<211> LENGTH: 405
<212> TYPE: DNA
<213> ORGANISM: Triticum aestivum

<400> SEQUENCE: 5

atgcagttgc ctagttatct tgctttcaaa ggcgacaatg ggaggttcct tggtgcgaag      60

atcgtcgagg gttatagata tcttgaatac tccaaagatg atattggaga tctaagtgtg     120
```

```
ttgcacacaa ttttcaccaa taaagatgga gttgtccgta taaaatccaa ctatttcgac    180

atgttttgga ggcgaagccc aaattggatc tgggctgatt caactgacac cacccacaac    240

aaccgtgata cattattcaa ggtgaccact gggcccgact tcattgctct gcgaaacttg    300

ggcaacaaca atttctgcaa aaggttaacc acagaaggga agtatgattg cctcaatgct    360

gctgttggtt ccatcacagc tgaagtaaaa atgcggtgca ttgaa                    405
```

<210> SEQ ID NO 6
<211> LENGTH: 288
<212> TYPE: DNA
<213> ORGANISM: Triticum aestivum

<400> SEQUENCE: 6

```
gatagtcaaa ttgttgaaaa catgaccacc acaacaaaca aaaccaaaat gatcttcaca     60

tacacaaata ccgtccagag tacctggagt tctactgttt cattgaagat tggcgtcaag    120

accaaattta aatccgggat tccatttgta gttgacggcg aagttgaggt cagcactgag    180

tttagtggat catatacctg ggggggagcc aaatctgaca caaaagtagt aagcaaacaa    240

attgatgttg aagttcctcc aatgaagaaa gtgacagtaa aagcgatt                 288
```

<210> SEQ ID NO 7
<211> LENGTH: 160
<212> TYPE: PRT
<213> ORGANISM: Triticum aestivum

<400> SEQUENCE: 7

```
Leu Pro Arg Cys Val Ala Leu Arg Ser Lys His Gly Asn Ser Tyr Leu
1               5                   10                  15

Arg Ser Val His Asp Lys Ser Gln Gly Gly Asn Phe Val Glu Leu Ser
            20                  25                  30

Ala Asp Asn Asp Gly Gly Val Met Asn Pro Arg Cys Arg Phe Tyr Leu
        35                  40                  45

Glu Ala Ser Lys Glu His Asp Gly Leu Val His Val Arg Cys Cys Tyr
    50                  55                  60

Asn Asn Lys Tyr Trp Ala Pro Gln Gln Arg Leu Leu His Gly Ser Ala
65                  70                  75                  80

Arg Trp Thr Ile Gly Thr Ala Asn Glu Leu Glu Glu Asp Leu Ser Lys
                85                  90                  95

Pro Ser Cys Thr Leu Phe Lys His Ile Pro Val Ser Gly Glu Asp Gly
            100                 105                 110

Ser Thr Cys Arg Phe Leu His Ser Gln Leu Gly Lys Tyr Ala Cys Val
        115                 120                 125

Leu Ser Ser Ser Asp Met Ser Lys His Pro Tyr Leu His Ile Ala Arg
    130                 135                 140

Glu Glu Ser Asp Gln Asp Asn Leu Leu Asp Ala Phe Thr Val Leu Asp
145                 150                 155                 160
```

<210> SEQ ID NO 8
<211> LENGTH: 135
<212> TYPE: PRT
<213> ORGANISM: Triticum aestivum

<400> SEQUENCE: 8

```
Met Gln Leu Pro Ser Tyr Leu Ala Phe Lys Gly Asp Asn Gly Arg Phe
1               5                   10                  15

Leu Gly Ala Lys Ile Val Glu Gly Tyr Arg Tyr Leu Glu Tyr Ser Lys
            20                  25                  30
```

-continued

Asp Asp Ile Gly Asp Leu Ser Val Leu His Thr Ile Phe Thr Asn Lys
        35                  40                  45

Asp Gly Val Val Arg Ile Lys Ser Asn Tyr Phe Asp Met Phe Trp Arg
    50                  55                  60

Arg Ser Pro Asn Trp Ile Trp Ala Asp Ser Thr Asp Thr Thr His Asn
65                  70                  75                  80

Asn Arg Asp Thr Leu Phe Lys Val Thr Thr Gly Pro Asp Phe Ile Ala
                85                  90                  95

Leu Arg Asn Leu Gly Asn Asn Asn Phe Cys Lys Arg Leu Thr Thr Glu
            100                 105                 110

Gly Lys Tyr Asp Cys Leu Asn Ala Ala Val Gly Ser Ile Thr Ala Glu
        115                 120                 125

Val Lys Met Arg Cys Ile Glu
    130                 135

<210> SEQ ID NO 9
<211> LENGTH: 78
<212> TYPE: PRT
<213> ORGANISM: Triticum aestivum

<400> SEQUENCE: 9

Phe Thr Tyr Thr Asn Thr Val Gln Ser Thr Trp Ser Ser Thr Val Ser
1               5                   10                  15

Leu Lys Ile Gly Val Lys Thr Lys Phe Lys Ser Gly Ile Pro Phe Val
            20                  25                  30

Val Asp Gly Glu Val Glu Val Ser Thr Glu Phe Ser Gly Ser Tyr Thr
        35                  40                  45

Trp Gly Gly Ala Lys Ser Asp Thr Lys Val Val Ser Lys Gln Ile Asp
    50                  55                  60

Val Glu Val Pro Pro Met Lys Lys Val Thr Val Lys Ala Ile
65                  70                  75

<210> SEQ ID NO 10
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 10
cgcaccaatg tggagtacag 20

<210> SEQ ID NO 11
<211> LENGTH: 19
<212> TYPE: DNA
<213> ORGANISM: Artificial Sequence
<220> FEATURE:
<223> OTHER INFORMATION: chemically synthesized oligonucleotide

<400> SEQUENCE: 11
catagaggcg gcagtaggg 19

<210> SEQ ID NO 12
<211> LENGTH: 19
<212> TYPE: DNA
<213> ORGANISM: Artificial Sequence
<220> FEATURE:
<223> OTHER INFORMATION: chemically synthesized oligonucleotide

<400> SEQUENCE: 12

-continued tgaccgtatg agcaaggag 19

<210> SEQ ID NO 13
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 13
ccagacaact cgcaacttag 20

<210> SEQ ID NO 14
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 14
atggcacacg ctacattgct 20

<210> SEQ ID NO 15
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 15
caacttcgcc gtcaactaca 20

<210> SEQ ID NO 16
<211> LENGTH: 22
<212> TYPE: DNA
<213> ORGANISM: Artificial Sequence
<220> FEATURE:
<223> OTHER INFORMATION: chemically synthesized oligonucleotide

<400> SEQUENCE: 16
cccttactct tccagcttga ga 22

<210> SEQ ID NO 17
<211> LENGTH: 22
<212> TYPE: DNA
<213> ORGANISM: Artificial Sequence
<220> FEATURE:
<223> OTHER INFORMATION: chemically synthesized oligonucleotide

<400> SEQUENCE: 17
ggaaagaggg acgtgcttaa at 22

<210> SEQ ID NO 18
<211> LENGTH: 22
<212> TYPE: DNA
<213> ORGANISM: Artificial Sequence
<220> FEATURE:
<223> OTHER INFORMATION: chemically synthesized oligonucleotide

<400> SEQUENCE: 18
cgcaccccta aaacccaaaa ta 22

<210> SEQ ID NO 19
<211> LENGTH: 22
<212> TYPE: DNA
<213> ORGANISM: Artificial Sequence -continued

```
<220> FEATURE:
<223> OTHER INFORMATION: chemically synthesized oligonucleotide

<400> SEQUENCE: 19

caactgcatc tgttctgaca ca                                              22


<210> SEQ ID NO 20
<211> LENGTH: 22
<212> TYPE: DNA
<213> ORGANISM: Artificial Sequence
<220> FEATURE:
<223> OTHER INFORMATION: chemically synthesized oligonucleotide

<400> SEQUENCE: 20

acatgaccac cacaacaaac aa                                              22


<210> SEQ ID NO 21
<211> LENGTH: 22
<212> TYPE: DNA
<213> ORGANISM: Artificial Sequence
<220> FEATURE:
<223> OTHER INFORMATION: chemically synthesized oligonucleotide

<400> SEQUENCE: 21

cctcacaggt gttcttcttt gg                                              22


<210> SEQ ID NO 22
<211> LENGTH: 480
<212> TYPE: DNA
<213> ORGANISM: Triticum aestivum

<400> SEQUENCE: 22

tttcaccaat aaagatggag ttgtccgtat aaaatccaac tatttcgaca tgttttggag      60

gcgaagccca aattggatct gggctgattc aactgacacc acccacaaca accgtgatac     120

attattcaag gtgaccactg ggcccgactt cattgctctg cgaaacttgg gcaacaacaa     180

tttctgcaaa aggttaacca cagaagggaa gtatgattgc ctcaatgctg ctgttggttc     240

catcacagct gaagtaaaaa tgcggtgcat tgaaccaatt gtttctcgag acatctatga     300

tgttgatttt cgcctaggtg aagctaagat ctacaccaat ggtattgagg gccttgatag     360

tcaaattgtt gaaaacatga ccaccacaac aaacaaaacc aaaatgatct tcacatacac     420

aaataccgtc cagagtacct ggagttctac tgtttcattg aagattggcg tcaagaccaa     480


<210> SEQ ID NO 23
<211> LENGTH: 480
<212> TYPE: DNA
<213> ORGANISM: Artificial Sequence
<220> FEATURE:
<223> OTHER INFORMATION: chemically mutated Triticum aestivum gene
      sequence

<400> SEQUENCE: 23

tttcaccaat aaagatggag ttgtccgtat aaaatccaac tatttcgaca tgttttggag      60

gcgaagccca aattggatct gggctgattc aactgacacc acccacaaca accgtgatac     120

attattcaag gtgaccactg ggcccgactt cattgctctg cgaaacttgg gcaacaacaa     180

tttctgcaaa aggttaacca cagaagggaa gtatgattgc ctcaatgctg ctgttggttc     240

catcacagct gaagtaaaaa tgcggtgcat tgaaccaatt gtttctcgag acatctatga     300

tgttgatttt cgcctaggtg aagctaagat ctacaccaat ggtattgagg gccttgatag     360

tcaaattgtt gaaaacatga ccaccacaac aaacaaaacc aaaatgatct tcacatacac     420
```

```
aaataccgtc cagagtacct agagttctac tgtttcattg aagattggcg tcaagaccaa    480


<210> SEQ ID NO 24
<211> LENGTH: 480
<212> TYPE: DNA
<213> ORGANISM: Artificial Sequence
<220> FEATURE:
<223> OTHER INFORMATION: chemically mutated Triticum aestivum gene
      sequence

<400> SEQUENCE: 24

tttcaccaat aaagatggag ttgtccgtat aaaatccaac tatttcgaca tgttttgaag     60

gcgaagccca aattggatct gggctgattc aactgacacc acccacaaca accgtgatac    120

attattcaag gtgaccactg ggcccgactt cattgctctg cgaaacttgg gcaacaacaa    180

tttctgcaaa aggttaacca cagaagggaa gtatgattgc ctcaatgctg ctgttggttc    240

catcacagct gaagtaaaaa tgcggtgcat tgaaccaatt gtttctcgag acatctatga    300

tgttgatttt cgcctaggtg aagctaagat ctacaccaat ggtattgagg gccttgatag    360

tcaaattgtt gaaaacatga ccaccacaac aaacaaaacc aaaatgatct tcacatacac    420

aaataccgtc cagagtacct ggagttctac tgtttcattg aagattggcg tcaagaccaa    480


<210> SEQ ID NO 25
<211> LENGTH: 418
<212> TYPE: PRT
<213> ORGANISM: Triticum aestivum

<400> SEQUENCE: 25

Asp Gly Leu Val His Val Arg Cys Cys Tyr Asn Asn Lys Tyr Trp Ala
1               5                   10                  15

Pro Gln Gln Arg Leu Leu His Gly Ser Ala Arg Trp Thr Ile Gly Thr
            20                  25                  30

Ala Asn Glu Leu Glu Glu Asp Leu Ser Lys Pro Ser Cys Thr Leu Phe
        35                  40                  45

Lys His Ile Pro Val Ser Gly Glu Asp Gly Ser Thr Cys Arg Phe Leu
    50                  55                  60

His Ser Gln Leu Gly Lys Tyr Ala Cys Val Leu Ser Ser Ser Asp Met
65                  70                  75                  80

Ser Lys His Pro Tyr Leu His Ile Ala Arg Glu Glu Ser Asp Gln Asp
                85                  90                  95

Asn Leu Leu Asp Ala Phe Thr Val Leu Asp Val Ser Glu Gln Met Gln
            100                 105                 110

Leu Pro Ser Tyr Leu Ala Phe Lys Gly Asp Asn Gly Arg Phe Leu Gly
        115                 120                 125

Ala Lys Ile Val Glu Gly Tyr Arg Tyr Leu Glu Tyr Ser Lys Asp Asp
    130                 135                 140

Ile Gly Asp Leu Ser Val Leu His Thr Ile Phe Thr Asn Lys Asp Gly
145                 150                 155                 160

Val Val Arg Ile Lys Ser Asn Tyr Phe Asp Met Phe Trp Arg Arg Ser
                165                 170                 175

Pro Asn Trp Ile Trp Ala Asp Ser Thr Asp Thr Thr His Asn Asn Arg
            180                 185                 190

Asp Thr Leu Phe Lys Val Thr Thr Gly Pro Asp Phe Ile Ala Leu Arg
        195                 200                 205

Asn Leu Gly Asn Asn Asn Phe Cys Lys Arg Leu Thr Thr Glu Gly Lys
    210                 215                 220
```

Tyr Asp Cys Leu Asn Ala Ala Val Gly Ser Ile Thr Ala Glu Val Lys
225 230 235 240

Met Arg Cys Ile Glu Pro Ile Val Ser Arg Asp Ile Tyr Asp Val Asp
245 250 255

Phe Arg Leu Gly Glu Ala Lys Ile Tyr Thr Asn Gly Ile Glu Gly Leu
260 265 270

Asp Ser Gln Ile Val Glu Asn Met Thr Thr Thr Thr Asn Lys Thr Lys
275 280 285

Met Ile Phe Thr Tyr Thr Asn Thr Val Gln Ser Thr Trp Ser Ser Thr
290 295 300

Val Ser Leu Lys Ile Gly Val Lys Thr Lys Phe Lys Ser Gly Ile Pro
305 310 315 320

Phe Val Val Asp Gly Glu Val Glu Val Ser Thr Glu Phe Ser Gly Ser
325 330 335

Tyr Thr Trp Gly Gly Ala Lys Ser Asp Thr Lys Val Val Ser Lys Gln
340 345 350

Ile Asp Val Glu Val Pro Pro Met Lys Lys Val Thr Val Lys Ala Ile
355 360 365

Gly Ser Asn Gly Leu Cys Asp Ile Pro Phe Ser Tyr Lys Gln Arg Asp
370 375 380

Ile Leu Thr Asn Gly Asp Glu Val Ile Gln Glu Phe Thr Asp Gly Met
385 390 395 400

Tyr Phe Gly Val Lys Thr Ser Ser Ile Thr Phe His Thr Lys Glu Glu
405 410 415

His Leu

<210> SEQ ID NO 26
<211> LENGTH: 300
<212> TYPE: PRT
<213> ORGANISM: Artificial Sequence
<220> FEATURE:
<223> OTHER INFORMATION: protein sequence from chemically mutated
Triticum aestivum gene

<400> SEQUENCE: 26

Asp Gly Leu Val His Val Arg Cys Cys Tyr Asn Asn Lys Tyr Trp Ala
1 5 10 15

Pro Gln Gln Arg Leu Leu His Gly Ser Ala Arg Trp Thr Ile Gly Thr
20 25 30

Ala Asn Glu Leu Glu Glu Asp Leu Ser Lys Pro Ser Cys Thr Leu Phe
35 40 45

Lys His Ile Pro Val Ser Gly Glu Asp Gly Ser Thr Cys Arg Phe Leu
50 55 60

His Ser Gln Leu Gly Lys Tyr Ala Cys Val Leu Ser Ser Ser Asp Met
65 70 75 80

Ser Lys His Pro Tyr Leu His Ile Ala Arg Glu Glu Ser Asp Gln Asp
85 90 95

Asn Leu Leu Asp Ala Phe Thr Val Leu Asp Val Ser Glu Gln Met Gln
100 105 110

Leu Pro Ser Tyr Leu Ala Phe Lys Gly Asp Asn Gly Arg Phe Leu Gly
115 120 125

Ala Lys Ile Val Glu Gly Tyr Arg Tyr Leu Glu Tyr Ser Lys Asp Asp
130 135 140

Ile Gly Asp Leu Ser Val Leu His Thr Ile Phe Thr Asn Lys Asp Gly
145 150 155 160

-continued

```
Val Val Arg Ile Lys Ser Asn Tyr Phe Asp Met Phe Trp Arg Arg Ser
                165                 170                 175

Pro Asn Trp Ile Trp Ala Asp Ser Thr Asp Thr Thr His Asn Asn Arg
            180                 185                 190

Asp Thr Leu Phe Lys Val Thr Thr Gly Pro Asp Phe Ile Ala Leu Arg
        195                 200                 205

Asn Leu Gly Asn Asn Asn Phe Cys Lys Arg Leu Thr Thr Glu Gly Lys
    210                 215                 220

Tyr Asp Cys Leu Asn Ala Ala Val Gly Ser Ile Thr Ala Glu Val Lys
225                 230                 235                 240

Met Arg Cys Ile Glu Pro Ile Val Ser Arg Asp Ile Tyr Asp Val Asp
                245                 250                 255

Phe Arg Leu Gly Glu Ala Lys Ile Tyr Thr Asn Gly Ile Glu Gly Leu
            260                 265                 270

Asp Ser Gln Ile Val Glu Asn Met Thr Thr Thr Thr Asn Lys Thr Lys
        275                 280                 285

Met Ile Phe Thr Tyr Thr Asn Thr Val Gln Ser Thr
    290                 295                 300


<210> SEQ ID NO 27
<211> LENGTH: 172
<212> TYPE: PRT
<213> ORGANISM: Artificial Sequence
<220> FEATURE:
<223> OTHER INFORMATION: protein sequence from chemically mutated
      Triticum aestivum gene

<400> SEQUENCE: 27

Asp Gly Leu Val His Val Arg Cys Cys Tyr Asn Asn Lys Tyr Trp Ala
1               5                   10                  15

Pro Gln Gln Arg Leu Leu His Gly Ser Ala Arg Trp Thr Ile Gly Thr
            20                  25                  30

Ala Asn Glu Leu Glu Glu Asp Leu Ser Lys Pro Ser Cys Thr Leu Phe
        35                  40                  45

Lys His Ile Pro Val Ser Gly Glu Asp Gly Ser Thr Cys Arg Phe Leu
    50                  55                  60

His Ser Gln Leu Gly Lys Tyr Ala Cys Val Leu Ser Ser Ser Asp Met
65                  70                  75                  80

Ser Lys His Pro Tyr Leu His Ile Ala Arg Glu Glu Ser Asp Gln Asp
                85                  90                  95

Asn Leu Leu Asp Ala Phe Thr Val Leu Asp Val Ser Glu Gln Met Gln
            100                 105                 110

Leu Pro Ser Tyr Leu Ala Phe Lys Gly Asp Asn Gly Arg Phe Leu Gly
        115                 120                 125

Ala Lys Ile Val Glu Gly Tyr Arg Tyr Leu Glu Tyr Ser Lys Asp Asp
    130                 135                 140

Ile Gly Asp Leu Ser Val Leu His Thr Ile Phe Thr Asn Lys Asp Gly
145                 150                 155                 160

Val Val Arg Ile Lys Ser Asn Tyr Phe Asp Met Phe
                165                 170
```

GENE ENCODING FHB1 RESISTANCE TO FUSARIUM HEAD BLIGHT DISEASE AND USES THEREOF

CROSS-REFERENCE TO RELATED APPLICATIONS

The present application is a continuation of U.S. Ser. No. 15/315,139, filed Nov. 30, 2016, which is the U.S. National Stage of International Patent Application No. PCT/US2015/033290, filed May 29, 2015, which claims the priority benefit of U.S. Provisional Patent Application Ser. No. 62/005,079, filed May 30, 2014, entitled GENE ENCODING FHB1 RESISTANCE TO FUSARIUM HEAD BLIGHT DISEASE AND USES THEREOF, each of which is incorporated by reference in its entirety herein.

FEDERALLY SPONSORED RESEARCH OR DEVELOPMENT

This invention was made with government support under contract numbers 59-0206-2-088, 59-0790-9-025, 59-0790-4-091, and 2004-35300-14787, awarded by the United States Department of Agriculture. The United States government has certain rights in the invention.

SEQUENCE LISTING

The following application contains a sequence listing in computer readable format (CRF), submitted as a text file in ASCII format entitled "Sequence Listing," created on May 27, 2015, as 29 KB. The content of the CRF filed is hereby incorporated by reference. Only one strand of each nucleic acid sequence is shown, but the complementary strand is understood as included by any reference to the displayed strand. The sequence of the complementary strand can be deduced as the reverse complement of the provided strand. SEQ ID NO:1 is the gene sequence of Fhb1 gene; SEQ ID NO:2 is the cDNA sequence for the Fhb1 gene. SEQ ID NO:3 is the 478 amino acid long protein sequence of Fhb1. SEQ ID NO:4 is the first conserved nucleic acid domain of the Agglutinin superfamily. SEQ ID NO:5 is the second conserved nucleic acid domain of the Agglutinin superfamily. SEQ ID NO:6 is the conserved nucleic acid domain of the ETX/MTX2 superfamily. SEQ ID NO:7 is the first conserved amino acid domain of the Agglutinin superfamily. SEQ ID NO:8 is the second conserved amino acid domain of the Agglutinin superfamily. SEQ ID NO:9 is the conserved amino acid domain of the ETX/MTX2 superfamily. SEQ ID NOS:10-13 are DNA primers used for real time quantitative PCR as described in the EXAMPLES section of this specification. SEQ ID NOS:14-15 are DNA primers used for Tilling as described in the EXAMPLES section of this specification. SEQ ID NOS:16-21 are DNA primers used for association studies as described in the EXAMPLES section of this specification. SEQ ID NOS:22-24 are mutant and R-NIL gene sequences shown aligned in FIG. 3. SEQ ID NOS:25-27 are mutant and R-NIL amino acid sequences shown aligned in FIG. 4.

BACKGROUND OF THE INVENTION

Field of the Invention

The present invention relates to methods and reagents for providing and/or enhancing resistance to *Fusarium* Head Blight disease (FHB), including genetically-modified plants having increased resistance to FHB.

Description of Related Art

FHB, also known as wheat scab, is a devastating disease caused by *Fusarium graminearum* (sexual stage, *Gibberella zeae*) that primarily affects small grain crops, including wheat and barley. Hot and humid weather conditions at anthesis promote spread of the disease, during which macroconidia spread at very fast rates and cause rapid secondary infections. From 1998-2000 the Midwestern United States suffered $2.7 billion in losses resulting from an FHB epidemic in wheat. FHB not only reduces crop production, it also severely affects grain quality due to the associated toxins (primarily De-oxynivalenol or DON). There thus exists a need in the art for improving the resistance of plants to FHB, particularly wheat, barley and other small grain crops. The present invention addresses that need.

SUMMARY OF THE INVENTION

The present invention provides genetically-modified plant cells having increased resistance to FHB disease relative to a control plant cell. In some embodiments, a genetically-modified plant of the invention comprises exogenous nucleic acid encoding a protein, or conserved domain or residue thereof, which confers resistance to FHB. In some embodiments, said exogenous nucleic acid encodes a protein, or conserved domain or residue thereof, which confers type 2 resistance to FHB and/or type 1 resistance to FHB. In some embodiments, said exogenous nucleic acid is an Fhb1 nucleic acid, or a plurality of copies of an Fhb1 nucleic acid, preferably an exogenous nucleic acid that encodes a protein comprising the amino acid sequence of SEQ ID NO:3, 7, 8, or 9; or a protein having at least about 70% amino acid identity with SEQ ID NO: 3, 7, 8, or 9 and retaining the functional characteristics of the protein having the amino acid sequence of SEQ ID NO:3, 7, 8, or 9, e.g., the ability to confer resistance to FHB. In some embodiments, the protein has antifungal activity, e.g., antifungal activity with respect to a species of *Fusarium*, e.g., a species selected from *F. avenaceum, F. bubigeum, F. culmorum, F. graminearum, F. langsethiae, F. oxysporum, F. poae, F. sporotrichioides, F. tricinctum, F. verticillioides*, and *F. virguliforme*.

In certain preferred embodiments, a genetically-modified plant cell of the invention comprises an exogenous nucleic acid that encodes a protein comprising the amino acid sequence of SEQ ID NO:3, 7, 8, or 9, or an exogenous nucleic acid that comprises (a) a nucleotide sequence of SEQ ID NO:1, 2, 4, 5 or 6; or (b) a nucleotide sequence having at least about 70% sequence identity to SEQ ID NO:1, 2, 4, 5 or 6; or (c) a polynucleotide that selectively hybridizes to a polynucleotide sequence corresponding to SEQ ID NO:1, 2, 4, 5 or 6. In some embodiments said protein has FHB1 activity. In some embodiments said exogenous nucleic acid is stably integrated into a chromosome in the nucleus of said plant cell. In some embodiments, said plant cell further comprises a second exogenous nucleic acid encoding a native resistance gene.

The present invention further provides transgenic plants and seeds comprising a plurality of plant cells as provided by the invention. In preferred embodiments, the transgenic plant or seed is selected from the group consisting of wheat and barley.

The present invention further provides a variety of methods, including methods for increasing tolerance to FHB infection in a plant that involve genetically modifying said plant to increase expression of FHB resistance activity relative to a control plant. In some embodiments the method comprises transforming said plant with an exogenous nucleic acid encoding a protein, or conserved domain or residue thereof, having FHB resistance activity, thereby increasing the tolerance of said plant to spread of an FHB-causing pathogen. Some embodiments result in stable incorporation of the exogenous nucleic acid into the transformed plant genome, and in some embodiments multiple copies of the exogenous nucleic acid sequence are transformed into the plant.

In certain preferred embodiments, methods for increasing tolerance to FHB infection in a plant involve transforming the plant with exogenous nucleic acid encoding a protein comprising the amino acid sequence of SEQ ID NO:3, 7, 8, or 9; or a protein having at least about 70% amino acid identity with SEQ ID NO:3, 7, 8, or 9 and retaining the functional characteristics of the protein having the amino acid sequence of SEQ ID NO:3. The functional characteristics of the protein preferably comprises the ability to confer resistance to FHB. In some embodiments the protein has antifungal activity. The exogenous nucleic acid preferably comprises (a) a nucleotide sequence of SEQ ID NO:1, 2, 4, 5 or 6; or (b) a nucleotide sequence having at least about 70% sequence identity to SEQ ID NO:1, 2, 4, 5 or 6.

The present invention also provides methods for producing a genetically-modified plant or seed having increased tolerance to FHB compared to a control plant that involve crossing a first parent plant with a second parent plant to thereby produce progeny, wherein at least one of the first or second parent plants is a transgenic plant of the invention. In some embodiments, the method further comprises pyramiding said exogenous nucleic acid with a native resistance gene.

The invention also provides methods of identifying a plant comprising at least one allele associated with FHB resistance activity in a plant that comprises: (a) screening genomic DNA from at least one plant for the presence of a nucleic acid marker that is associated with FHB resistance activity; and (b) selecting at least one plant comprising an allele of at least one of said nucleic acid markers. In some embodiments the nucleic marker is selected from the group consisting of SEQ ID NO:1, nucleotide sequences having at least 90% sequence identity to SEQ ID NO:1, and contiguous fragments of nucleotide sequences having at least 90% sequence identity to SEQ ID NO:1. In some embodiments, the plant whose genomic DNA is screened in step (a) and/or the at least one plant selected in step (b) is a plant from a population generated by a cross. In certain preferred embodiments, the method is applied to wheat or barley.

In one or more embodiments of the invention, the markers of resistance include an Fhb1 gene having SEQ ID NO:1, sequences having at least 90% sequence identity to SEQ ID NO:1, and sequences having at least 50% sequence identity SEQ ID NO:1, wherein there is at least 95% identity in residues 69-377, 2330-2734, or 2816-3103 of SEQ ID NO:1. In one or more embodiments, the markers of resistance are selected from the group consisting of: nucleic acid sequences comprising, consisting, or consisting essentially of SEQ ID NO:4, 5, or 6, and nucleic acid sequences encoding a protein comprising, consisting, or consisting essentially of SEQ ID NO:7, 8, or 9. The method further comprises selecting plants having one or more of these markers of resistance. The invention is also broadly concerned with uses of Fhb1 encoded nucleic acids for control of FHB disease, including, but not limited to producing genetically-modified plants having increased resistance to FHB as compared to a control plant. In some embodiments, the genetically-modified plants comprise one or more copies of exogenous nucleic acid encoding a protein or conserved domain or residue having type 2 resistance (resistance to the spread of the pathogen after initial infection) of FHB. The genetically-modified plants having type 2 resistance can also comprise nucleic acid encoding a protein or conserved domain or residue having type 1 resistance to FHB (resistance to initial infection of FHB).

The invention further provides nucleic acids, including isolated nucleic acids comprising a sequence selected from the group consisting of: (a) a polynucleotide sequence at least 70% identical to SEQ ID NO:1; (b) a polynucleotide sequence at least 70% identical SEQ ID NO:2, 4, 5 or 6; (c) a polynucleotide sequence encoding a polypeptide at least 70% identical to SEQ ID NO:3, 7, 8, or 9; (d) a polynucleotide sequence at least 70% identical to bases 69-377 of SEQ ID NO:1; (e) a polynucleotide sequence at least 70% identical to bases 2330-2734 of SEQ ID NO:1, (f) a polynucleotide sequence at least 70% identical to bases 2816-3103 of SEQ ID NO:1 (g) a polynucleotide sequence at least 70% identical to bases 19-498 of SEQ ID NO:2; (h) a polynucleotide sequence at least 70% identical to bases 511-915 of SEQ ID NO:2; (i) a polynucleotide sequence at least 70% identical to bases 997-1284 of SEQ ID NO:2; (j) a polynucleotide sequence encoding a polypeptide at least 70% identical to residues 7-166 of SEQ ID NO:3; (k) a polynucleotide sequence encoding a polypeptide at least 70% identical to residues 171-305 of SEQ ID NO:3; (l) a polynucleotide sequence encoding a polypeptide at least 70% identical to residues 351-428 of SEQ ID NO:3; (m) a polynucleotide sequence encoding a polypeptide fragment consisting of at least 25 contiguous amino acid residues of SEQ ID NO: 3, 7, 8, or 9; (n) a polynucleotide that selectively hybridizes to a polynucleotide sequence corresponding to SEQ ID NOS: 1, 2, 4, 5 or 6; and (o) complements of a polynucleotide selected from the group consisting of the polynucleotides identified herein as (a)-(n), with the proviso that said sequence is not identical to SEQ ID NO:1, or any contiguous fragment of SEQ ID NO:1.

An isolated nucleic acid of the invention preferably a protein retaining the functional characteristics of the protein having the amino acid sequence of SEQ ID NO:3. The functional characteristics of the protein preferably comprises the ability to confer resistance to FHB, e.g., through an antifungal activity.

In certain preferred embodiments, an isolated nucleic acid of the invention comprises a polynucleotide sequence at least 95% identical to SEQ ID NO:1, 2, 4, 5 or 6, preferably a polynucleotide sequence selected from the group consisting of SEQ ID NO:2, 4, 5 or 6.

In general, the present invention includes any and all kinds of manipulation of the Fhb1 nucleic acids provided herein, including, without limitation, by means of genetic engineering techniques to modify the gene, increase copy number or increased expression, gene-based markers for breeding and pyramiding with other genes for increased FHB resistance. For example fusion proteins or vectors encoding for fusion proteins for increased FHB resistance, according to the sequences described herein, in combination with other desirable wheat characteristics are contemplated by the present invention.

The present invention also provides recombinant vectors that incorporate an isolated nucleic acid of the invention. In some embodiments the isolated nucleic acid is operably linked to a heterologous promoter. In certain preferred embodiments the heterologous promoter is functional in plants and/or is induced by a pathogen, particularly a plant pathogen. In some preferred embodiments, the isolated nucleic acid comprises a polynucleotide sequence at least 95% identical to SEQ ID NO:1, 2, 4, 5 or 6, e.g., a polynucleotide sequence selected from the group consisting of SEQ ID NO:2, 4, 5 or 6. In some embodiments the isolated nucleic acid encodes a fusion protein.

The present invention also provides polypeptides, including isolated polypeptides comprising an amino acid sequence at least about 70% identical to SEQ ID NO:3, SEQ ID NO:7, SEQ ID NO:8, or SEQ ID NO:9. In some embodiments, the amino acid sequence of a polypeptide of the invention is at least 95% identical to SEQ ID NO:3, SEQ ID NO:7, SEQ ID NO:8, or SEQ ID NO:9, e.g., an amino acid sequence selected from the group consisting of SEQ ID NO:3, 7, 8 or 9.

In certain preferred embodiments, a polypeptide of the invention substantially retains the functional characteristics of a polypeptide having an amino acid sequence selected from the group consisting of SEQ ID NO:3, 7, 8 or 9, e.g., the polypeptide has FHB1 activity. In preferred embodiments the polypeptide has antifungal activity, such as antifungal activity towards a species of *Fusarium*, e.g., a species selected from *F. avenaceum, F. bubigeum, F. culmorum, F. graminearum, F. langsethiae, F. oxysporum, F. poae, F. sporotrichioides, F. tricinctum, F. verticillioides*, and *F. virguliforme*. In some embodiments, a polypeptide of the invention is a fusion protein.

The present invention provides methods for producing an FHB-resistant plant that comprises: (a) performing marker assisted selection to identify a plant possessing a resistance allele of Fhb1; and (b) generating a progeny of said plant wherein said progeny possesses said resistance allele of Fhb1 exhibits at least partial resistance to FHB. In some embodiments, the method produces an FHB-resistant elite plant. In some embodiments, marker assisted selection is conducted using an assay selected from the group consisting of single base extension (SBE), allele-specific primer extension sequencing (ASPE), DNA sequencing, RNA sequencing, microarray-based analyses, universal PCR, allele specific extension, hybridization, mass spectrometry, ligation, extension-ligation, and Flap Endonuclease-mediated assays. In some embodiments, a plant produced using a method provided by this aspect of the invention further comprises one or more traits selected from the group consisting of herbicide tolerance, increased yield, insect control, fungal disease resistance, virus resistance, nematode resistance, bacterial disease resistance, mycoplasma disease resistance, modified oils production, high oil production, high protein production, germination and seedling growth control, enhanced animal and human nutrition, lower raffinose, environmental stress resistance, increased digestibility, production of industrial enzymes, production of pharmaceutical proteins, production of pharmaceutical peptides, production of pharmaceutical small molecules, improved processing traits, improved flavor, improved nitrogen fixation, improved hybrid seed production, reduced allergenicity, and improved production of biopolymers and biofuels. In some embodiments the resulting plant is resistant to a herbicide selected from the group consisting of glyphosate, dicamba, glufosinate, sulfonylurea, bromoxynil, 2,4-Dichlorophenoxyacetic acid, and norflurazon.

The invention further provides methods of producing an FHB-resistant plant that comprise the step of transferring a nucleic acid comprising a nucleic acid of the invention, e.g., an Fhb1 nucleic acid, to an FHB-susceptible plant, wherein said transfer of said nucleic acid is performed by transformation, by crossing, by protoplast fusion, by a doubled-haploid technique or by embryo rescue. In some embodiments, such a method further comprises steps of: detecting a marker associated with FHB-resistance in said plant; and selecting a FHB-resistant plant comprising said nucleic acid. In certain preferred embodiments, the FHB-susceptible plant is selected from the group consisting of wheat or barley. In some embodiments, the transfer of nucleic acid further comprises steps of: crossing said FHB-resistant plant with an FHB-susceptible plant to produce offspring plants; and selecting from among the offspring plants a plant that comprises in its genome an exogenous Fhb1 nucleic acid. Such selection can comprise marker-assisted selection with a marker associated with FHB1 activity. In some embodiments, an FHB-resistant plant, or a part thereof, produced by a method of the invention will have a susceptibility to FHB that is at least 3 times lower than a susceptible control plant of the same species; wherein the hybrid plant contains an Fhb1 nucleic acid and wherein said Fhb1 nucleic acid is not in the natural genetic background of the FHB-resistant plant.

The invention further provides FHB-resistant plants, and parts thereof, that comprise within their genome an Fhb1 nucleic acid, wherein said an Fhb1 nucleic acid is not in the natural genetic background of said FHB-resistant plant. In some embodiments, the invention provides a hybrid FHB-resistant plant, or part thereof, produced by crossing an FHB-resistant plant of the invention with another plant that exhibits commercially desirable characteristics, wherein the hybrid plant contains an Fhb1 nucleic acid and wherein said Fhb1 nucleic acid is not in the natural genetic background of the FHB-resistant plant.

The present invention also provides seeds produced by growing a plant of the invention, wherein the seed contains an Fhb1 nucleic acid and wherein said Fhb1 nucleic acid is not in the natural genetic background of the FHB-resistant plant. In preferred embodiments, seeds, plants and plant parts provided by the invention are selected from the group consisting of wheat and barley.

The present invention also provides methods for identifying a plant that comprises a genotype associated with a FHB-resistance, comprising: detecting in said plant a DNA polymorphism in an Fhb1 locus associated with FHB-resistance, and selecting said plant from a population of plants, wherein the selected plant comprises a genotype associated with FHB-resistance, and wherein the selected plant or progeny thereof exhibit FHB-resistance. In preferred embodiments, the plant is selected from the group consisting of wheat and barley.

The present invention also provides plants comprising a heterologous recombinant expression cassette, wherein the plant has enhanced FHB-resistance compared to a control plant lacking the expression cassette, the expression cassette comprising a promoter operably linked to a polynucleotide, which polynucleotide, when expressed, increases expression of an FHB1 protein compared to a control plant lacking the expression cassette, wherein increased expression of the FHB1 protein results in enhanced FHB-resistance compared to the control plant. In some embodiments, the polynucleotide encodes a polypeptide comprising an amino acid sequence at least 70% identical to any of SEQ ID NO:3, 7, 8 or 9, wherein said polypeptide has FHB1 activity. The invention further provides methods of making such plants that preferably comprise a step of introducing the expression cassette into a plurality of plants; and selecting a plant that expresses the polynucleotide from the plurality of plants. In some embodiments, the selecting step comprises selecting a plant that has enhanced FHB-resistance.

The present invention also provides methods for reducing the production of pathogen-associated toxins in a plant that involve genetically modifying said plant to increase expression of FHB resistance activity relative to a control plant. In some embodiments, the method comprises transforming said plant with an exogenous nucleic acid encoding a protein, or conserved domain or residue thereof, having FHB resistance activity, thereby reducing the production of pathogen-associated toxins in said plant. In certain preferred embodiments, the exogenous nucleic acid encodes a protein comprising the amino acid sequence of SEQ ID NO:3, 7, 8, or 9; or a protein having at least about 70% amino acid identity with SEQ ID NO:3, 7, 8, or 9 and retaining the functional characteristics of the protein having the amino acid sequence of SEQ ID NO:3, e.g., the ability to confer resistance to FHB. In certain preferred embodiments, the exogenous nucleic acid comprises (a) a nucleotide sequence of SEQ ID NO:1, 2, 4, 5 or 6; or (b) a nucleotide sequence having at least about 70% sequence identity to SEQ ID NO:1, 2, 4, 5 or 6. In some embodiments, the toxin is selected from the group consisting of fumonisins and trichothecenes, particularly De-oxynivalenol (DON).

BRIEF DESCRIPTION OF THE DRAWINGS

FIG. 3. Clustal Omega gene sequence alignment of the mutant plants as compared to wild type resistant lines. The G>A mutations have been highlighted in grey.

FIG. 4. Clustal Omega protein alignment of the mutant plants compared to wild type protein. Tryptophan>stop codon mutations in the mutants have been highlighted in grey.

DETAILED DESCRIPTION OF PREFERRED EMBODIMENTS

Figure 1:
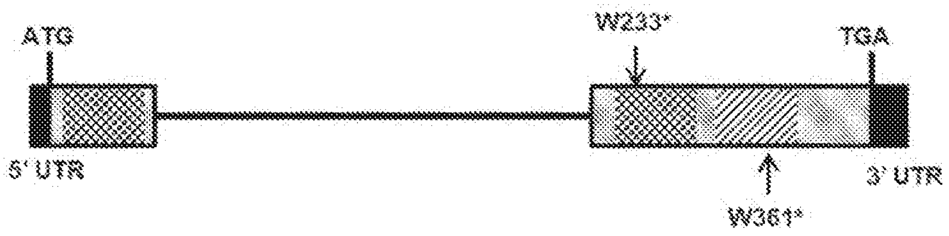
FIG. 1. Gene structure of Fhb1. Grey boxes show the exons, and connecting black lines show the introns. Checkered regions of exon 1 and 2 depict the Agglutinin superfamily domains, and upward diagonal region of exon 2 shows ETX/MTX2 domain. Black boxes at the ends show the untranslated region at 5' and 3' ends. Arrows indicate the position of stop codon in the two identified mutants.

In some embodiments, the invention provides proteins, nucleic acids, and nucleic acid constructs, plasmids and vectors capable of improving the disease resistance of a plant. As used herein, the term "capable of improving the disease resistance of a plant" denotes that the protein or nucleic acid will, at least when present in certain contexts, provide some improvement with respect to resistance to a disease. Whether there is actual improvement in any given context, and the extent of improvement, can vary depending upon the particular plant, strain or cultivar, the genetic background, the presence of the other genetic traits, and/or environmental factors. In other words, transgenic or genetically-modified plants according to the invention are plants having improved disease resistance relative to corresponding control plants grown under the same growing conditions. Such plants are referred to herein as "resistant" plants.

Other embodiments of the invention include plants having improved disease resistance. Some embodiments of the invention provide methods for improving the disease resistance of plants, and methods useful in the production of reagents and methods for providing plants with improved resistance to disease. In some embodiments of the invention these methods employ nucleic acids, proteins and/or other reagents provided by various aspects of this invention.

Unless otherwise indicated by the context, references herein to a "plant" or "plants" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

In various embodiments, the invention is suitable for use with a variety of plants, including both monocotyledons (i.e., plants having one cotyledon (seed-leaf), aka "monocots") and dicotyledons (i.e., plants having two cotyledons, aka "dicots"). Non-limiting examples of plants suitable for the disclosed embodiments include grains (e.g., wheat, oat, barley, rice, maize, millet, rye, sorghum, triticale, buckwheat, quinoa), legumes (e.g., soybeans, beans, peas, alfalfa), tubers (e.g., potatoes, sweet potatoes, cassava, yam), and the like. In certain preferred embodiments the plant is a grain, most preferably wheat or barley, or a wheat or barley cultivar.

In preferred embodiments, the disease is fungal in origin. In particular preferred embodiments, the disease is *Fusarium* Head Blight Disease (FHB). More generally, enhanced resistance to any fungal pathogen is contemplated, including fungal pests such as species of *Fusarium, Sclerotinia, Botrytis, Cercospora, Gibberella, Oidium, Phytophthora, Sephoria, Verticillium, Alternaria, Cladisporium, Rhizoctonia, Ustilago*, or *Puccinia*. In preferred embodiments, targeted fungal pathogen is a species of *Fusarium*, e.g., a species selected from *F. avenaceum, F. bubigeum, F. culmorum, F. graminearum, F. langsethiae, F. oxysporum, F. poae, F. sporotrichioides, F. tricinctum, F. verticillioides*, and *F. virguliforme*.

In some embodiments, the invention encompasses polypeptides and nucleic acids that are not identical to any of the explicitly disclosed nucleotide or amino acid sequences, but instead may be only "substantially identical" to a reference sequence, e.g., one of the sequences explicitly described herein. As explained below, these substantially identical variants are specifically covered by the terms "Fhb1 nucleic acid" (or "Fhb1 polynucleotide") and "FHB1 protein" (or "FHB1 polypeptide").

Nucleic acids or proteins "comprising" a nucleotide sequence or amino acid sequence means that the entire sequence is present, but may include one or more additional nucleotides or amino acids on the 3' or 5' end of the designated sequence, as long as the sequence retains the functional characteristics of the gene or protein. Nucleic acids or proteins "consisting of" a nucleotide sequence or amino acid sequence means that the entire sequence is present, and no further nucleotides or amino acids are encompassed by the nucleic acid or protein.

A "control" plant, as used in the present invention, refers to a plant used to compare against transgenic or genetically-modified plants according to the invention for the purpose of identifying changes in the transgenic or genetically-modified plant. The control plant is of the same species as the non-naturally occurring plant. In some cases, the control plant may be a wild-type (native) plant, although cultivars and genetically altered plants that otherwise have normal disease resistance can also be used a references for comparison. A "wild-type" plant is a plant that has not been genetically modified or treated in an experimental sense. A "wild-type" gene is one that has the characteristics of a gene isolated from a naturally occurring source. A "wild-type" gene product is one that has the characteristics of a gene product isolated from a naturally occurring source, whereas "modified" genes or gene products are those having modifications in sequence and/or functional properties (i.e., altered characteristics) when compared to the wild-type gene or gene product. The term "transgenic" is used herein to refer to a plant, a plant structure, a plant cell, a plant tissue, or a plant seed that contains at least one heterologous gene in one or more of its cells. Likewise, "genetically-modified", "modified," or "transformed," cells, tissues, seeds, plants, etc. are those that have been altered to include a transgene expressing exogenous gene products, as opposed to non-modified cells, tissues, etc. The terms are synonymous with "genetically-engineered."

The term gene "expression" is used herein to refer to the process of converting genetic information encoded in a gene into RNA (e.g., mRNA, rRNA, tRNA, or snRNA) through transcription of the gene (i.e., via the enzymatic action of an RNA polymerase), and into protein, through translation of mRNA. Gene expression can be regulated at many stages in the process. The term "overexpression" refers to the production of a gene product in transgenic plants that exceeds levels of production in normal, control, or non-transgenic plants. References to altered "levels" of expression refers to the production of gene product(s) in modified plants, such as transgenic plants, in amounts or proportions that differ from that of normal, control, or non-modified plants.

The term "operably linked" refers to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced The term "vector" refers to nucleic acid molecules that transfer DNA segment(s) from one cell to another. The term includes recombinant DNA molecules containing a desired coding sequence(s) and appropriate nucleic acid sequences (e.g., promoters) necessary for the expression of the operably linked coding sequence in a particular host organism. It is used interchangeably herein with the term "plasmid." Examples of suitable vectors for used in the invention include pACH20, pJL10P5, pGmubi, pACH17, and the like.

The term "transform" is used herein to refer to the introduction of foreign DNA into cells. Transformation may be accomplished by a variety of means known to the art and described herein.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from naturally occurring allelic variants.

An "expression cassette" refers to a nucleic acid construct, which when introduced into a host cell, results in transcription and/or translation of a RNA or polypeptide, respectively. Antisense constructs or sense constructs that are not or cannot be translated are expressly included by this definition.

The term "isolated" when used in relation to a nucleic acids or proteins, refers to sequences that are identified and separated from at least one contaminant nucleotide or amino acid with which it is ordinarily associated in its natural environment. That is, an isolated nucleic acid or protein is one that is present in a form or setting that is different from that in which it is found in nature.

The terms "sequence identity" or "amino acid identity" are used herein to describe the sequence relationships between two or more nucleic acid or amino acid sequences when aligned for maximum correspondence over a specified comparison window. The percentage of "identity" is determined by comparing two optimally aligned sequences over the comparison window. For "optimal alignment" of the two sequences, it will be appreciated that the portion of the sequence in the comparison window may include gaps (e.g., deletions or additions) as compared to the reference sequence, which does not contain additions or deletions. After alignment, the number of matched positions (i.e., positions where the identical nucleic acid base or amino acid residue occurs in both sequences) is determined and then divided by the total number of positions in the comparison window. This result is then multiplied by 100 to calculate the percentage of sequence or amino acid identity. It will be appreciated that a sequence having a certain percentage of sequence identity to a reference sequence does not necessarily have to have the same total number of nucleotides or amino acids. Thus, a sequence having a certain level of "identity" includes sequences that correspond to only a portion (i.e., 5' non-coding regions, 3' non-coding regions, coding regions, etc.) of the reference sequence.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

In preferred embodiments of the invention, an FHB1 protein has "FHB1 activity," and an "Fhb1 nucleic acid" encodes a protein having "FHB1 activity." The term "FHB1 activity" refers to the FHB-resistance functionality provided by the FHB1 protein having the amino acid sequence of SEQ ID NO:3, and/or the FHB-resistance functionality provided by a protein encoded by SEQ ID NO:1 and/or SEQ ID NO:2. The degree of FHB1 activity conferred by an FHB1 protein or FHB1 nucleic acid of the invention can vary, and the invention contemplates FHB1 proteins and nucleic acids having FHB1 activity greater than, or less than, the protein encoded by SEQ ID NO:3, so long as the protein and/or nucleic acid provides some not insubstantial enhancement of disease resistance relative to a control plant. The extent of resistance can vary depending upon a variety of external factors, including the presence of other resistance-conferring genes, the overall genetic background, and environmental factors. In preferred embodiments of the invention, an FHB1 protein has antifungal activity. In certain preferred embodiments the antifungal activity inhibits a species of *Fusarium*, e.g., a species selected from *F. avenaceum, F. bubigeum, F. culmorum, F. graminearum, F. langsethiae, F. oxysporum, F. poae, F. sporotrichioides, F. tricinctum, F. verticillioides*, and *F. virguliforme*.

In cases where a polynucleotide sequence of the invention is transcribed and translated to produce a functional polypeptide, one of skill will recognize that because of codon degeneracy a number of polynucleotide sequences will encode the same polypeptide. These variants are specifically covered by the terms "Fhb1 nucleic acid," "Fhb1 polynucleotide" and their equivalents. In addition, the terms specifically include those full length sequences substantially identical and/or substantially similar (determined as described below) to an Fhb1 polynucleotide sequence and that encode proteins that retain the function of the FHB1polypeptide (e.g., resulting from conservative substitutions of amino acids in the FHB1 polypeptide).

Two nucleic acid sequences or polypeptides are said to be "identical" if the sequence of nucleotides or amino acid residues, respectively, in the two sequences is the same when aligned for maximum correspondence as described below. The terms "identical" or "percent identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The term "absolute percent identity" refers to a percentage of sequence identity determined by scoring identical amino acids as 1 and any substitution as zero, regardless of the similarity of mismatched amino acids. In a typical sequence alignment, e.g., a BLAST alignment, the "absolute percent identity" of two sequences is presented as a percentage of amino acid "identities." As used herein, where a sequence is defined as being "at least X % identical" to a reference sequence, e.g., "a polypeptide at least 90% identical to SEQ ID NO:3," it is to be understood that "X % identical" refers to absolute percent identity, unless otherwise indicated. In cases where an optimal alignment of two sequences requires the insertion of a gap in one or both of the sequences, an amino acid residue in one sequence that aligns with a gap in the other sequence is counted as a mismatch for purposes of determining percent identity. Gaps can be internal or external, i.e., a truncation.

The term "substantial identity" of polynucleotide sequences means that a polynucleotide comprises a sequence that has at least 25% sequence identity. Alternatively, percent identity can be any integer from at least 25% to 100% (e.g., at least 25%, 26%, 27%, 28%, . . . , 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%). Some embodiments include at least: 25%, 30%, 35%, 40%, 45%, 50%, 55%, 60%, 65%, 70%, 75%, 80%, 85%, 90%, 95%, or 99% identity compared to a reference sequence using the programs described herein; preferably BLAST using standard parameters, as described below. The present invention provides for polynucleotides that are at least substantially identical to SEQ ID NO:1, 2, 4, 5 or 6. One of skill will recognize that these values can be appropriately adjusted to determine corresponding identity of proteins encoded by two nucleotide sequences by taking into account codon degeneracy, amino acid similarity, reading frame positioning and the like.

"Substantial identity" of amino acid sequences for these purposes normally means sequence identity of at least 40%. The percent identity of polypeptides can be any integer from at least 40% to 100% (e.g., at least 40%, 41%, 42%, 43%, . . . , 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%). Some embodiments include at least 60%, 65%, 70%, 75%, 80%, 85%, 90%, 95%, or 99% identity. The present invention provides for polypeptides that are at least substantially identical to SEQ ID NOS3, 7, 8 or 9.

Amino acid substitution matrices and their use in quantifying the similarity between two sequences are well-known in the art. A high similarity generally correlates with homology of the sequences. The BLOSUM62 matrix is often used as a default scoring substitution matrix in sequence alignment protocols such as Gapped BLAST 2.0. The gap existence penalty is imposed for opening gap in one of the aligned sequences, and the gap extension penalty is imposed for each amino acid position in the gap. Thus, a two amino acid residue gap will result in a penalty of 13, 11 for existence of the gap and 2 for extending the gap two amino acids. The alignment is defined by the amino acid positions of each sequence at which the alignment begins and ends, and optionally by the insertion of a gap or multiple gaps in one or both sequences, so as to arrive at the highest possible score. While optimal alignment and scoring can be accomplished manually, the process is facilitated by the use of a computer-implemented alignment algorithm, e.g., gapped BLAST 2.0. To generate accurate similarity scores using NCBI BLAST, it is important to turn off any filtering, e.g., low complexity filtering, and to disable the use of composition based statistics. One should also confirm that the correct substitution matrix and gap penalties are used. Optimal alignments, including multiple alignments, can be prepared using, e.g., PSI-BLAST.

One of skill in the art will recognize that two polypeptides can also be "substantially identical" if the two polypeptides are immunologically similar. Thus, overall protein structure may be similar while the primary structure of the two polypeptides display significant variation. Therefore a method to measure whether two polypeptides are substantially identical involves measuring the binding of monoclonal or polyclonal antibodies to each polypeptide. Two polypeptides are substantially identical if the antibodies specific for a first polypeptide bind to a second polypeptide with an affinity of at least one third of the affinity for the first polypeptide.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. When a "comparison window" is used to determine the percent identity between two sequences, a lower limit on the length of the comparison window can be imposed, e.g., a minimum length of 20, 30, 40, 50, 60, 70, 80, 90, 100, 110, 120, 130, 140, 150, 160, 170, 180, 190, 200, 210, 220, 230, 240 or 250 amino acids. Alternatively, percent identity can be defined such that the window of comparison over which the percent identity criterion is satisfied must include a sufficient amount of the reference sequence to possess some FHB1 activity. Thus, if two sequences satisfy a minimum percent identity criterion (e.g., at least 90% sequence identity) only over a window of comparison that is less than the entire length of the amino acid sequence used as a reference (e.g., SEQ ID NO:3), then the subsequence of the reference sequence corresponding to the window of comparison must itself have FHB1 activity in order to conclude that the two sequences meet the percent identity criterion. For example, if two sequences only share X percent identity over a short window of comparison (e.g., 20 contiguous amino acids), and that 20 contiguous amino acids is not sufficient unto itself to possess FHB1 activity (which would normally be the case), then the two sequences do not satisfy the criterion of possessing at least X percent identity. Alternatively, if the window of comparison spans a longer subsequence of contiguous amino acids that possesses FHB1 activity even without the rest of the sequence, the criterion will be found to have been met.

Methods of alignment of sequences for comparison are well-known in the art. Optimal alignment of sequences for comparison can be conducted, e.g., using a computerized implementation of a homology or similarity alignment algorithm, or by manual alignment and visual inspection. Examples of a useful algorithms in this regard include, but are not limited to, BLAST and PILEUP.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program typically uses as defaults a word length (W) of 11, the BLOSUM62 scoring matrix, alignments (B) of 50, expectation (E) of 10, M=5, N=−4, and a comparison of both strands.

The BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for Methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (O);
4) Arginine (R), Lysine (K);
5) Isoleucine (I), Leucine (L), Methionine (M), Valine (V); and
6) Phenylalanine (F), Tyrosine (Y), Tryptophan (W).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA). The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions In certain preferred embodiments, the invention provides an FHB1 protein having the amino acid sequence of SEQ ID NO:3 ("wild-type FHB1 protein"). As used herein, the terms "protein" and "polypeptide" are used interchangeably, unless otherwise indicated by context. In some embodiments, the protein comprises, consists of, or consists essentially of the full amino acid sequence of SEQ ID NO:3, while in other embodiments the protein comprises some contiguous fragment or fragments of the amino acid sequence of SEQ ID NO:3. In preferred embodiments, the protein is capable of improving the disease resistance of a plant. In some particularly preferred embodiments, the protein substantially retains the full functionality of the full-length protein encoded by SEQ ID NO:3, while in other embodiments the protein only partially retains the functionality of the full-length protein. In some embodiments, the invention provides a protein with an improved ability to confer disease resistance compared to wild-type FHB1 protein.

In some embodiments, the invention provides conserved functional domains present in the full-length FHB1 protein. Two of these conserved domains, i.e., the Agglutinin superfamily domains, fall within the Agglutinin superfamily, and are present at amino acid residue positions 7-166, and 171-305 in SEQ ID NO:3. The amino acid sequences of the Agglutinin superfamily domains are provided separately as SEQ ID NOS:7 and 8. The Agglutinin superfamily includes proteins like *Amaranthus caudatus* agglutinin, which is a lectin. Although the biological function of *Amaranthus caudatus* agglutinin is unknown, the protein has a high binding specificity for the methyl-glycoside of the T-antigen, which is linked to serine or threonine residues of cell surface glycoproteins. *Amaranthus caudatus* agglutinin is comprised of a homodimer, with each homodimer consisting of two beta-trefoil domains.

Another conserved functional domain, i.e., the ETX/MTX2 superfamily domain, falls within the ETX/MTX2 superfamily, and is present at amino acid residue positions 351-428 in SEQ ID NO:3. The amino acid sequence of the ETX/MTX2 superfamily domain is provided separately as SEQ ID NO:9. The ETX/MTX2 superfamily includes Epsilon toxin (ETX), which is produced by *Clostridium perfringens* type B and D strains, and Mosquitocidal toxin (MTX2) which is produced by *Bacillus sphaericus*. ETX and MTX2 are pore forming toxins that attach to the plasma membranes of a host and produce toxins that lead to altered permeability and ion-efflux, resulting in cell death.

Based on analysis of the amino acid sequence of FHB1, the mechanism by which the FHB1 protein improves disease resistance is predicted to involve the Agglutinin superfamily domain recognizing and identifying the cell surface of a pathogen, especially fungal pathogen, and the ETX/MTX2 superfamily domain forming a pore in the membrane that kills the pathogen. Protein subcellular localization prediction software LOCTREE 3 predicts that FHB1 protein is secreted outside cells after production, which is consistent with the proposed mode of action.

The invention also provides in certain embodiments other proteins that are not identical to any of the proteins identified above, e.g., protein variants, but that share some degree of homology with one or more of the proteins identified above, preferably a relatively high degree of homology. In preferred embodiments, a homologous protein of the invention retains some, or, more preferably, substantially all of the functional characteristics of wild-type FHB1 protein, or a functional fragment of wild-type FHB1 protein, including but not limited to the agglutinin superfamily domain and/or the ETX/MTX2 superfamily domain. Such homologous proteins generally share at least 65% sequence identity with the disclosed sequences, preferably at least 75%, or at least 85%, or at least 95%, and even more preferably at least 99%. In particular, minor substitutions, deletions, and the like can be introduced at one or more amino acid positions in the disclosed sequences without departing from the scope of the invention, so long as the altered sequence maintains functionality, e.g., the disease resistance activity of the unaltered sequence.

In some preferred embodiments, a homologous protein of the invention retains a relatively high identity in amino acid residues corresponding to one or more of the conserved functional domains found in wild-type FHB1 protein, e.g., the agglutinin superfamily domain and/or the ETX/MTX2 superfamily domain. For example, in preferred embodiments the amino acid residues corresponding to one or more of these functional domains are identical to the corresponding sequences found in wild-type FHB1 protein, or at least share a relatively high degree of identity, preferably at least 75%, or at least 85%, or at least 95%, and even more preferably at least 99%. By maintaining a relatively high degree of homology in these regions, the retention of desired functionality can often be enhanced. Conversely, undue departure from wild-type amino acid sequence in conserved functional domains can increase the likelihood of loss of functionality.

Functional protein variants of the invention can be produced by any of a variety of techniques known in the art, including site-directed mutagenesis, DNA shuffling, and/or directed evolution. If retention of function is desired, conservative amino acid substitutions are generally preferred. In other embodiments, alteration of function is the desired objective, in which case non-conservative substitutions can be appropriate.

In some embodiments, the invention provides nucleic acids capable of improving disease resistance in a plant. As used herein, the terms "nucleic acid," "polynucleotide," and "DNA" are used interchangeably, unless indicated otherwise by context. In some embodiments, a nucleic acid or protein of the invention is "isolated." As used herein, the term "isolated" refers to a synthesized, cloned, and/or truncated sequence from the naturally occurring sequence.

In a preferred embodiment, the nucleic acid comprises, consists of, or consists essentially of a nucleic acid having the nucleotide sequence of SEQ ID NO:1 (corresponding to genomic Fhb1 sequence), the nucleotide sequence of SEQ ID NO:2 (corresponding to the Fhb1 cDNA sequence), the nucleotide sequence of SEQ ID NO:4 (corresponding to the sequence encoding first agglutinin superfamily conserved domain, i.e., bases 69-377 of SEQ ID NO:1, which is equivalent to bases 19-498 of SEQ ID NO:2), SEQ ID NO:5 (corresponding to the sequence encoding the second agglutinin superfamily conserved domain, i.e., bases 2330-2734 of SEQ ID NO:1, which is equivalent to bases 511-915 of SEQ ID NO:2), and/or SEQ ID NO:6 corresponding to the sequence encoding the ETX/MTX2 superfamily conserved domain, i.e., bases 2816-3103 of SEQ ID NO:1, which is equivalent to bases 997-1284 of SEQ ID NO:2).

In some embodiments, the invention provides nucleic acids that encode one or more of the proteins of the invention, as described above. In certain preferred embodiments, the invention provides isolated nucleic acid sequences encoding a protein comprising, consisting, or consisting essentially of SEQ ID NO:3, 7, 8 or 9. The invention also provides fragments and complements of the nucleic acids described elsewhere herein, as well as non-identical but homologous nucleic acid sequences, e.g., substantially identical sequences. Unless otherwise indicated, reference to a nucleic acid sequence also encompasses its complement. Such sequences typically share at least 65% sequence identity with sequences disclosed herein, including SEQ ID NO: 1, 2, 4, or 5, nucleic acid sequences encoding a protein comprising, consisting, or consisting essentially of SEQ ID NO: 3, 6, or 7. More preferably, a nucleic acid of the invention shares at least 75% identity, still more for preferably at least 80%, 85%, 90%, or 95%, and even more preferably at least 99% identity with one or more of the aforementioned nucleic acid sequences. In particular, minor substitutions, deletions, and the like can be introduced at one or more positions in the disclosed sequences without departing from the scope of the invention, so long as the altered sequence maintains functionality, e.g., encoding a protein having the disease resistance activity of the unaltered sequence.

The invention further provides nucleic acid constructs, including vectors, plasmids and expression cassettes, comprising at least one nucleic acid sequence of the invention as described above. In preferred embodiments, a nucleic acid construct of the invention is recombinant and/or isolated. In some embodiments of the invention the nucleic acid construct comprises a nucleotide sequence of SEQ ID NO:1, 2, 4, 5 and/or 6, or a fragment thereof. In preferred embodiments, the nucleic acid construct comprises a nucleotide sequence encoding a protein capable of improving disease resistance of a plant, such as a protein comprising, consisting, or consisting essentially of SEQ ID NO:3, 7, 8 or 9. In some embodiments a nucleic acid construct of the invention comprises a promoter sequence and/or regulatory element. Preferably, the promoter sequence is operably linked to a nucleic acid sequence encoding a protein capable of improving disease resistance of a plant, such as a protein comprising, consisting, or consisting essentially of SEQ ID NO:3, 7, 8 or 9.

The term "promoter" or "regulatory element" refers to a region or sequence determinants located upstream or downstream from the start of transcription and which are involved in recognition and binding of RNA polymerase and other proteins to initiate transcription. Promoters need not be of plant origin, for example, promoters derived from plant viruses, such as the CaMV35S promoter, can be used in the present invention. Suitable promoters include constitutive promoters, as well as promoters responsive to the presence of disease and/or infection, particularly FHB. Non-limiting examples of promoters include maize ubiquitin promoters, high molecular weight (HMW) glutenin promoter subunit (Dy10), the CaMV35S promoter, the soybean GMubi3 promoter, and/or rice actin promoter. In some preferred embodiments, a pathogen-induced and/or disease-induced promoter can be used to promote elevated expression in response to exposure to a pathogen or disease. Examples of pathogen-induced promoters include the pathogen-induced PRP1 gene promoter and the inducible promoter for the maize PRms gene, whose expression is induced by the pathogen *Fusarium moniliforme.*

In some embodiments, the invention provides plants having improved disease resistance. Improved disease resistance can be assessed by comparison with a control plant, wherein the disease resistance of the control plant has not been modified or improved by methods or reagents provided by various aspects of the present invention. In some embodiments of the invention, the plant is a genetically modified plant that has been altered by the introduction of exogenous nucleic acid encoding a protein capable of conferring disease resistance. In preferred embodiments of the invention, the exogenous nucleic acid comprises, consists, or consists essentially of one of the nucleic acids provided herein, and/or encodes one of the proteins provided herein.

The term "exogenous" is used herein to refer to a nucleic acid sequence (e.g., DNA, RNA), gene, or protein that originates from a source outside of (i.e., foreign to) the host plant into which it is introduced to create the transgenic plant. For example, the term as it is used in reference to expression of an encoding nucleic acid, refers to introduction of an exogenous encoding nucleic acid in an expressible form into the host plant. In other words, the nucleic acid is not native to and/or has not been derived from that particular plant. In contrast, the term "endogenous" is used herein interchangeably with "native" and refers to nucleic acid sequences, genes, gene products, proteins, etc. that are naturally associated with or found in a control or wild-type plant.

In one or more embodiments, the exogenous nucleic acid encoding the thermostable starch synthase protein is also heterologous. The term "heterologous" refers to genetic material derived from a source other than the referenced species, and is contrasted with "homologous," which refers to genetic material derived from, naturally associated with, or native to, the species of the host plant (although not necessarily to the host plant itself). For example, in some embodiments of the invention, the transgenic plants are created by introducing genetic material encoding a protein conferring disease resistance, e.g., FHB1, from one species into a host plant of a different species, wherein the host plant expresses that heterologous gene product. Thus, since an exogenous nucleic acid molecule is heterologous with respect to the host plant, the transformed plant cells will contain transcripts of the nucleic acid molecules introduced that would not be detected in a control plant qualitatively or quantitatively (e.g., by PCR). If, on the other hand, an exogenous nucleic acid molecule is homologous with respect to the host plant, the transformed plants can be distinguished from control plants based upon additional expression of transcripts, which can be detected using "quantitative" PCR techniques.

In the present invention, it is in some cases advantageous to introduce an endogenous and/or heterologous nucleic acid encoding a protein conferring disease resistance, e.g., FHB1 protein, derived from a first plant having relatively high disease resistance into a second plant with respect to which enhanced disease resistance is desired. In some embodiments the first plant and second plant are different species, while in other embodiments they are different strains or cultivars of the same species. The disease resistance encoding sequence can be isolated from the first plant, or synthesized based upon available genetic information. Advantageously, expression or overexpression of the exogenous and/or heterologous nucleic acid increases the disease resistance of the transformed second plant.

Transformation techniques for plants are well known in the art and include any technique involving the uptake of exogenous genetic material by the plant, such as particle bombardment-mediated delivery, *Agrobacterium*-mediated techniques, PEG- or electroporation-mediated uptake, viral infection, and/or microinjection.

In some embodiments, the invention provides nucleic acids and other reagents useful for genotyping and/or selecting plants having and/or expressing a nucleic acid encoding disease resistance, e.g., Fhb1 or one of the other nucleic acids provided by the invention having the same or similar functional characteristics. These nucleic acids can be useful in a variety of contexts, including as molecular markers for breeding.

In certain embodiments, the invention provides genetically-modified plants having improved disease resistance. In some cases, these genetically-modified plants have been engineered to incorporate a nucleic acid of the invention encoding a protein capable of conferring disease resistance, e.g., Fhb1. In some embodiments, the nucleic acid is operatively coupled with a promoter and/or other transcription regulating elements, which can be cis or trans with respect to the protein encoding nucleic acid. In some preferred embodiments, the nucleic acid is incorporated into a genetic construct, such as a cassette and/or expression vector or plasmid. In some preferred embodiments, the nucleic acid is stably integrated into the plant chromosome.

In some embodiments, a plant provided by the invention incorporates a nucleic acid sequence not native to plant, e.g., an exogenous Fhb1 nucleic acid derived from another plant, strain or cultivar. In some embodiments, a plant of the invention incorporates modifications to its own native gene encoding disease resistance that enhance or modify function. For example, techniques for DNA editing, such as site-directed mutagenesis or CRISPR, can be used to modify a gene like Fhb1, or an Fhb1 homologue, or an allelic variant of Fhb1, for improved function. The specific mutations can be based on information gleaned from methods provided by this invention, such as the use of known techniques to identify variations in the gene that correlate with improved function.

In some embodiments of the invention, the disease resistance of a plant is enhanced by increasing expression of a disease resistance encoding nucleic acid such as Fhb1. This can be accomplished, for example, by introducing an expression cassette of the invention with a promoter and/or other transcription regulatory elements that promote relatively high levels of expression. In other embodiments, it can be accomplished by modifying the promoter and/or transcription regulatory elements already present in the plant, or by introducing new promoter and/or transcription regulatory elements into the plant for increased expression. In other embodiments, increased expression can be achieved by introducing more than one copy of the nucleic acid into a plant. These and other techniques for increasing expression can be used individually or in combination to achieve higher levels of FHB1 activity, by elevated expression of Fhb1, or some other disease resistance conferring gene, relative to a control plant.

In some embodiments, the invention provides a variety of methods for improving disease resistance in plants, preferably, but not exclusively, grains such as wheat or barley. For example, the invention provides methods for genetically modifying a plant by introducing a nucleic acid encoding disease resistance, e.g., Fhb1 or one of the other nucleic acids provided by the invention. The genetic modification can be transgenic, i.e., introduction of a nucleic acid not native to the plant, e.g., a gene derived from another plant that does not interbreed with the target plant, for a synthetic gene. In some embodiments, the genetic modification can be cisgenic, in which case the nucleic acid is derived from a closely related plant that could be conventionally bred with the target plant. In preferred embodiments, the protein encoding nucleic acid sequence is operably linked to a promoter and/or other transcription regulating elements. In preferred embodiments, the nucleic acid sequence is stably integrated into the chromosome.

In some embodiments of the invention, multiple copies of a disease resistance conferring nucleic acid, such as Fhb1, are introduced into a plant in order to increase expression levels. In a variety of preferred embodiments, a nucleic acid of the invention, such as an Fhb1 nucleic acid, is stacked and/or pyramided with other desired genes and genetic traits, optionally including genes that confer resistance to a disease or diseases such as FHB. For example, a preferred allelic variant of FHB, which can be identified using methods of this invention, is pyramided with other genes contributing towards disease resistance or other useful traits.

In some methods provided by the invention, an exogenous and/or heterologous promoter, or other transcription regulatory element, is introduced into a plant in an operable relationship with a gene capable of conferring disease resistance, such as Fhb1, or another nucleic acid provided herein, so as to increase expression of FHB resistance. In some embodiments, the promoter and/or transcription regulatory elements are induced by a disease state or by presence of a pathogen, e.g., the FHB pathogen.

In some embodiments, expression of a native Fhb1 gene is induced or enhanced by a technology referred to as "endogenous gene activation" (EGA). EGA can be accomplished, for example, by means of a vector comprising one or more regulatory sequences functional in the plant with respect to which increased expression is desired. Such regulatory sequences may be, for example, promoters or enhancers. The regulatory sequence may then be introduced into the desired locus of the genome by homologous recombination, thus operably linking the regulatory sequence with the gene, the expression of which is to be induced or enhanced. In some preferred embodiments, a vector useful for EGA includes targeting sequences corresponding to portions of the endogenous gene such that, after a step of homologous recombination, the regulatory sequence will be appropriately targeted to provide endogenous gene activation.

In some embodiments, the invention provides methods for editing the genome of a plant to improve disease-resistance including gene editing techniques based on CRISPR technology, as described above. In some embodiments, a native disease-resistance gene is edited to improve functionality. For example, a native gene such as a first Fhb1 allele can be edited to incorporate one or more genetic variations found to be present in a second Fhb1 allele, as in a case where the second allele is found to confer a higher degree of resistance.

In some embodiments, the invention provides methods for reducing the production of pathogen-associated toxins by increasing the disease tolerance of the plant using the methods described herein. Toxins addressed by various embodiments of the invention include fumonisins and trichothecenes. In particular, the invention provides methods for genetically modifying plants to render them more resistant to *Fusarium* infection, thereby reducing the level of De-oxynivalenol (DON) and other toxins associated with *Fusarium*. In preferred embodiments, these methods involve genetically modifying the plant for increased disease resistance with respect to a disease that creates toxins, using methods described herein. The invention also encompasses plants generated by these methods, including plants having a reduced susceptibility to toxin buildup relative to a control plant. In particularly preferred embodiments, the plant is barley or wheat. This aspect of the invention is particularly useful for reducing DON content in barley products used by the barley malting in brewing industries. Nucleic acids provided by the invention can be introduced in barley as a means for reducing DON content in barley products, either transgenically or by breeding strategies.

In some embodiments, the invention provides methods for identifying allelic variants with improved functionality. In other embodiments, the invention provides methods for identifying genetic markers for disease resistance, which can be useful in procedures such as marker-assisted selection (MAS). In some embodiments, a genetic marker of the invention can be useful for identifying the presence of an Fhb1 gene, or more generally a nucleic acid encoding an FHB1 protein, an Fhb1/FHB1 variant, an Fhb1/FHB1 homolog, or an allelic variant having FHB1 activity. In other embodiments, a genetic marker of the invention can be useful for identifying the presence of an allelic variant of an Fhb1 gene or homolog, preferably an allelic variant with greater disease resistance functionality than one or more other national occurring alleles. In other embodiments, a genetic marker of the invention can be useful for identifying the presence of a transcription regulatory element, e.g., a promoter capable of inducing enhanced expression of disease resistance. The transcription regulatory element can be cis or trans in relation to a gene capable of conferring disease resistance, such as Fhb1.

In some embodiments the invention provides methods for using the disclosed Fhb1 gene sequence information to identify plants that contain the Fhb1 gene for use in breeding programs. Currently, breeders rely on closely located markers which sometimes recombine leading to failure of the breeding programs. The Fhb1 gene can be pyramided with other native resistance genes to enhance the level of resistance in wheat cultivars. In addition, multiple copies of the genes can be introduced by appropriate breeding strategies to increase the resistance in plants.

In other embodiments, the invention provides methods for using genetic markers of the invention for genotyping plants, preferably so as to identify plants having a genotype capable of conferring enhances disease resistance relative to a control plant. In some embodiments, such genotyping is used for breeding improved disease-resistance into a plant of interest, using a methodology such as marker assisted selection (MAS). These methods can be used to improve Fhb1-conferred disease resistance, for example, or for stacking or pyramiding enhanced Fhb1-conferred disease resistance with other desired genes and/or traits.

In various embodiments, methods of the invention include culturing plant tissue (e.g., leaf, cotyledon, or hypocotyl explants) on a suitable media (e.g., Murashige and Skoog (MS), supplemented media, etc.) followed by introduction of the exogenous nucleic acid into the tissue using suitable techniques. The exogenous nucleic acid can be introduced using a construct, vector, plasmid or other suitable technique. Expression of the nucleotide sequence results in transformed or modified tissue. Reporter genes and/or selection media can be used to select for and verify transformation. The transformed tissue can then be used to regenerate transgenic whole plants having increased disease resistance. Transgenic plants can be regenerated using various techniques depending upon the plant species involved. In one or more embodiments, regeneration comprises inducing callus formation from the transformed tissue, and regeneration of shoots, followed by rooting of the shoots in soil or other appropriate rooting media to generate the whole plant.

The resulting transgenic plants can be crossed to prepare progeny, and preferably homozygous progeny or seeds. Thus, disease-resistant plants (e.g., FHB-resistant wheat or barley) can also be produced indirectly by breeding parent plants having increased disease-resistance with other disease-resistant plants, or even with other cultivars having additional desired characteristics (e.g., pest or herbicide resistance, geographic adaptation, stalk strength, he tolerance, etc.). The resulting progeny can then be screened to identify progeny having increased disease-resistance.

Plants of the present invention include a plant that has a resistance level of from 1 to 5, 1 being completely immune, 2 being resistant to substantially resistant, 3 being mid-resistant to partially resistant, 4 being mid-susceptible, and 5 being susceptible, when assayed for resistance or susceptibility to FHB by any method amenable to the numerical scale described herein.

In a preferred aspect, the present invention provides a plant to be assayed for resistance or susceptibility to FHB by any method to determine whether a plant has a resistance level of from 1 to 5, 1 being completely immune, 2 being resistant to substantially resistant, 3 being mid-resistant to partially resistant, 4 being mid-susceptible, and 5 being susceptible, according to the numerical scale described herein.

In light of the impact of FHB on yield, another aspect of the present invention provides plants and derivatives thereof of with a nucleic acid encoding FHB-resistance that exhibit increased grain yield in the presence of FHB compared to a control plant.

A nucleic acid encoding FHB-resistance of the present invention may be introduced into an elite inbred plant line, preferably an elite inbred wheat line or an elite inbred barley line. An "elite line" is any line that has resulted from breeding and selection for superior agronomic performance. An elite plant is a representative plant from an elite variety.

An FHB-resistance gene of the present invention may also be introduced into an elite plant comprising one or more transgenes conferring herbicide tolerance, increased yield, insect control, fungal disease resistance, virus resistance, nematode resistance, bacterial disease resistance, mycoplasma disease resistance, modified oils production, high oil production, high protein production, germination and seedling growth control, enhanced animal and human nutrition, low raffinose, environmental stress resistant, increased digestibility, industrial enzymes, pharmaceutical proteins, peptides and small molecules, improved processing traits, improved flavor, nitrogen fixation, hybrid seed production, reduced allergenicity, biopolymers, and biofuels among others. In one aspect, the herbicide tolerance is selected from the group consisting of glyphosate, dicamba, glufosinate, sulfonylurea, bromoxynil and norflurazon herbicides. These traits can be provided by methods of plant biotechnology as transgenes.

An FHB-resistance allele or alleles can be introduced from any plant that contains that allele (donor) to any recipient plant. In one aspect, the recipient plant can contain an additional FHB-resistance loci. In another aspect, the recipient plant can contain a transgene. In another aspect, while maintaining the introduced FHB-resistance allele or alleles, the genetic contribution of the plant providing the disease resistance can be reduced by back-crossing or other suitable approaches. In one aspect, the nuclear genetic material derived from the donor material in the plant can be less than or about 50%, less than or about 25%, less than or about 13%, less than or about 5%, 3%, 2% or 1%, but that genetic material contains the FHB-resistance locus of interest.

In some embodiments, plants containing one or more FHB-resistance loci can act as donor plants. Plants containing FHB-resistance loci can be, for example, screened for by using a nucleic acid molecule capable of detecting a marker of polymorphism associated with resistance.

In one or more embodiments, the invention is also concerned with a process of producing seed. In some embodiments, the method comprises self-pollination of a genetically-modified plant as described herein. In some embodiments, the method comprises crossing a first plant with a second plant, wherein at least one of the first or second plants is a genetically-modified plant having increased disease resistance, particularly with respect to FHB, as described herein. In some embodiments, the first and second plants are both genetically modified plants having increased disease-resistance, as described herein. In one or more embodiments, the first and second plants can be crossed via cross-pollination using insects (e.g., flies in cloth cages), manual (hand) pollination, and the like. Genetic modification can be cisgenic or transgenic, or the product of gene editing.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

EXAMPLES

The following examples set forth methods in accordance with the invention. It is to be understood, however, that these examples are provided by way of illustration and nothing therein should be taken as a limitation upon the overall scope of the invention.

Introduction

*Fusarium* Head Blight (FHB), also known as wheat scab, is a very destructive disease of wheat, and limited sources of resistance are known against it. Hot and humid weather conditions at anthesis are conducible for the spread of the disease, during which macroconidia spread at very fast rates causing rapid secondary infections. The "Fhb1 QTL" is a quantitative trait locus from Chinese Landrace Sumai3' that provides resistance to the spread of *Fusarium graminearum* infection. Due to large and consistent contribution towards resistance against scab, the Fhb1 QTL is the most widely used source of resistance in breeding programs. There are numerous strains of *Fusarium*, but the Fhb1 QTL provides horizontal resistance against all the isolates of *Fusarium*, therefore screenings for FHB resistance are done using fairly aggressive strains of *F. graminearum.*

Screening for resistance to FHB is a resource intensive exercise and needs to be replicated over different locations, necessitating marker-assisted selection in breeding programs. Cloning of Fhb1 gene facilitates the development of perfect markers for utilization in breeding programs and gene pyramiding for increasing the level of resistance in germplasm. Understanding of the mode of action of the gene will be very useful for combating scab in wheat, barley, and other affected cereals.

Resistant and susceptible near isogenic lines were used for gene expression studies due to the similarity expected in their genetic background. The susceptible NIL was found to be missing this gene, whereas expression of the gene was found to increase by two-fold in the resistant NIL, 96 hours after inoculation. Numerous transcriptomic studies have been done for identifying the candidate gene by various groups using these two near isogenic lines. Most of the gene expression studies for FHB have been conducted up to 96 hours post-inoculation, as the fungal growth is arrested at about the same period after infection in resistant lines.

TILLING, which is a powerful reverse genetic technique, was used to validate the cloned gene, because of the uniformity of genetic background of the mutants and control. Ethyl methane sulphonate (EMS) is an alkylating agent and has been reported to mostly cause G>A/C>T transitions in wheat. Our results of the TILLING experiment were also in agreement, as not even a single transversion (G>T/C>A) was observed in the sequenced mutants. After screening 1932 plants, 40 mutants were identified with a product of 926 bp, giving an average mutation frequency of 1/39.9 mutation/kb, which is similar to other reports of mutation frequencies in hexaploid bread wheat TILLING populations. Two independent non-sense mutations were identified among the selected mutant plants, where Tryptophan amino acids were mutated to premature stop codons at positions 233 and 361 in the second agglutinin domain and ETX/MTX2 domain respectively, of the protein.

Phenotyping of the two mutants along with S-NIL and R-NIL controls was done in the greenhouse according to the described procedure. Scoring and photography was done 21 days after inoculation. In both the independent mutants loss of resistance due to premature truncation of the FHB1 protein was observed, proving beyond doubt that the gene cloned in this study is Fhb1.

Example 1

Plant Materials and FHB Assays

Resistant and susceptible near isogenic lines (R-NIL and S-NIL) were used for expression profiling studies. *Fusarium graminearum* strain K3639 was used for inoculation. *F. graminearum* was cultured on mung bean broth at 25° C. shaken at 100 rpm. At anthesis, $10^{th}$ spikelet of the spikes to be tested were inoculated with 10 µl macroconidial suspension at a concentration of $10^5$ macroconidia/ml. The inoculated spikes were covered with moisture-saturated ziplock bags for 72 hours. For RNA extraction the inoculated spikelet and adjacent spikelets were harvested at appropriate intervals after inoculations. Disease scoring was done 21 days after inoculations.

Example 2

Gene Annotation and Gene Structure Determination

A Bacterial Artificial Chromosome (BAC) library developed from Sumai 3 was used to search for the candidate gene. The BAC Library was screened with markers from Chinese Spring Fhb1 region to delineate putative candidate gene. Gene annotation and gene structure determination was done using FGENESH and BLASTx searches. NCBI conserved domain search module was used for determining conserved domains of the gene.

Example 3

Real-Time Quantitative PCR (qPCR)

Total RNA was extracted using TRIZOL reagent (Invitrogen, Carlsbad, Calif., USA) and RNA quantification was done with Nanodrop-1000 (Thermo Scientific). RNA quality was determined using Bioanalyzer (Agilent Technologoies, USA). First strand cDNA was synthesized using the SuperScript™ first strand cDNA synthesis kit (Invitrogen, Carlsbad, Calif., USA) using 5 µg total RNA. Quantitative PCR was carried out on Biorad CFX96 real time PCR detection system using iQ™ SYBR® Green Supermix (BioRad, Hercules, USA). The PCR cycle used for qPCR was 95° C.-3 minutes, 44 cycles of 95° C.-15 seconds and 60° C.-lminute with plate read at every step, and 95° C.-10". At the end of the cycle, melt curve analysis was done to confirm specificity of products. All reactions were carried out in three technical replicates over three biological replicates. Actin was used as internal reference control. The following primers were used for qPCR reactions: Fhb1 gene forward primer (5'-CGCACCAATGTGGAGTACAG-3' (SEQ ID NO:10)); Fhb1 gene reverse primer (5'-CATAGAGGCGGCAGTAGGG-3' (SEQ ID NO:11)); Actin gene forward primer (5'-TGACCGTATGAGCAAGGAG-3' (SEQ ID NO:12)); Actin gene reverse primer (5'-CCAGACAACTCGCAACTTAG-3' (SEQ ID NO:13)). The $2^{-\delta\delta CT}$ method was used to calculate the transcript values of the samples. Changes in expression level were calculated as compared to 0 hours of inoculation.

Example 4

Protein Structure Determination

Protein sequence predicted from the gene sequence was used to determine the 3D structure of the gene using Protein Homology/analogy Recognition Engine V 2.0 (PHYRE 2.0, http://www.sbg.bio.ic.ac.uk/phyre2). Software JMOL (http://jmol.sourceforge.net/) was used to view the structure of the protein.

Example 5

Validation of the Cloned Gene

Targeting Induced Local Lesions in Genome (TILLING) approach was used to validate the cloned gene. Seeds of R-NIL were treated with ethyl methanesulfonate (EMS), which is a chemical mutagen mostly causing transitions (G>A and C>T mutations) in DNA. These seeds gave rise to M1 plants, which were allowed to self-pollinate, yielding M2 seeds. A TILLING population of 1,932 individuals was developed by growing one M2 seed per M1 plant. The DNA of all the M2 individuals was extracted using Qiagen Biosprint DNA extraction system. The DNA was normalized and 4× pooling was done. PCRs were done using the following gene specific primers spanning the conserved domain of the gene: Fhb1 gene forward primer (5'-ATGGCACACGCTACATTGCT-3' (SEQ ID NO:14)); Fhb1 gene reverse primer (5'-CAACTTCGCCGTCAACTACA-3' (SEQ ID NO:15)). A touchdown profile (95° C.-5 minutes, 6 cycles of 95° C.-1 minute, 58-56° C.-1 minute with a decrease of 0.5° C. per cycle, 72° C.-1 minute 15 seconds, followed by 30 cycles of 95° C.-1 minute, 54° C.-1 minute, 72° C.-1 minute 15 seconds, and a final extension of 72° C.-7 minutes) was used. PCR products were subsequently denatured and slowly reannealed to form heteroduplexes between mismatched DNA (95° C.-2 minutes, 5 cycles of 95° C.-01 second, 95-85° C.-1 minute with a decrease of 2° C. per cycle, and 60 cycles of 85-25° C.-10 seconds). Home-made Cel-I endonuclease was extracted from celery and optimized using a SURVEYOR Mutation Detection Kit (Cat. No. 706020, Transgenomic Inc., Omaha, Nebr., USA). Two µl of Cel-I was added to the heteroduplexed products and incubated at 45° C. for 45 minutes. Reactions were stopped using 2.5 µl 0.5M EDTA. The digested products were visualized on 2% agarose gels. Mutants could be identified as those products that showed cleaved bands in addition to the full-length, uncleaved production. Forty mutants were found in the TILLING pools. A total of 40 mutants were found on 4× pools of the entire population screened. Selected pools were deconvoluted to identify mutant individuals which were then sequenced by Sanger sequencing. Sequence analysis was done using Clustal Omega (www.clustal.org) for sequence alignment and the protein translate tool of ExPASy (www.expasy.org).

Example 6

Antifungal Activity of Fhb1 Protein

The protein was extracted from pre-anthesis spikes of resistant near isogenic line (R-NIL). Twenty spikes of R-NIL were collected at pre-anthesis stage, and ground using liquid nitrogen. The protein was extracted using 400 ml of 0.15M NaCl for 16 hours at 4° C. on a magnetic stirrer. Ammonium sulphate precipitation of protein was done at 35% saturation by shaking for 2 hours at 4° C., which was followed by centrifuging at 17,000 g for 20 minutes. The precipitate was dissolved in 40 ml 0.15M NaCl. Extensive dialysis was done against 0.15M NaCl using a dialysis tubing of cutoff value 6-8 kDaltons. The dialysate was then further purified by affinity chromatography. Briefly, a chromatography column was 20% filled with chitin powder, and equilibriated with 0.15M NaCl. The dialysate was applied to the column and the column was washed 0.01 Tris-Cl pH 8.5 containing 1M NaCl to remove unbound proteins until the OD 280 absorbance was lower than 0.05. The column was again washed twice with 0.01 Tris-Cl pH 8.5 without NaCl. To elute the protein, 1M Glacial acetic acid was used. The eluate was dialysed again using 0.15 M NaCl to remove the eluants. The purified protein was then used to check the antifungal activity on a potato dextrose agar plate with 48 hours of fungal inoculation at 72° C. using ~10 macroconidia of *Fusarium graminearum* strain 3639. This experiment was done in five replications. Four sterile filter disks were placed on the plate at ~3 cm distance from the mycelia. Eighty microliters of the extracted protein was applied to the filter disks along with positive control (0.15M glucose solution), mock control (0.15M NaCl solution), and negative control (0.1% fungicide Prosaro). After 72 hours, growth of mycelia was recorded.

Example 7

Association Studies of the Gene

For association mapping the Fhb1 gene was sequenced from 41 varieties of wheat from China, Japan and USA with known FHB reaction. The following primer sequences were used for sequencing different parts of the gene. Fhb1-Exon1 forward primer (5'-CCCTTACTCTTCCAGCTTGAGA-3' (SEQ ID NO:16)); Fhb1-Exon1 reverse primer (5'-GGAAAGAGGGACGTGCTTAAAT-3' (SEQ ID NO:17)); Fhb1-Exon2-part1 forward primer (5'-CGCACCCCTAAAACCCAAAATA-3' (SEQ ID NO:18)); Fhb1-Exon2-part1 reverse primer (5'-CAACTGCATCTGTTCTGACACA-3' (SEQ ID NO:19)); Fhb1-Exon2-part2 forward primer (5'-ACATGACCACCACAACAAACAA-3' (SEQ ID NO:20)); Fhb1-Exon2-part2 reverse primer (5'-CCTCACAGGTGTTCTTCTTTGG-3' (SEQ ID NO:21)). A touchdown profile (95° C.-5 minutes, 6 cycles of 95° C.-1 minute, 67° C.-1 minute with a decrease of 1° C. per cycle, 72° C.-1 minute 30 seconds, followed by 30 cycles of 95° C.-1 minute, 60° C.-1 minute, 72° C.-1 minute 30 seconds, and a final extension of 72° C.-7 minutes) was used for PCR. The products were run on agarose gels and sequenced using the Sanger sequencing approach.

Results and Discussion

1. Gene Structure

Figure 2:
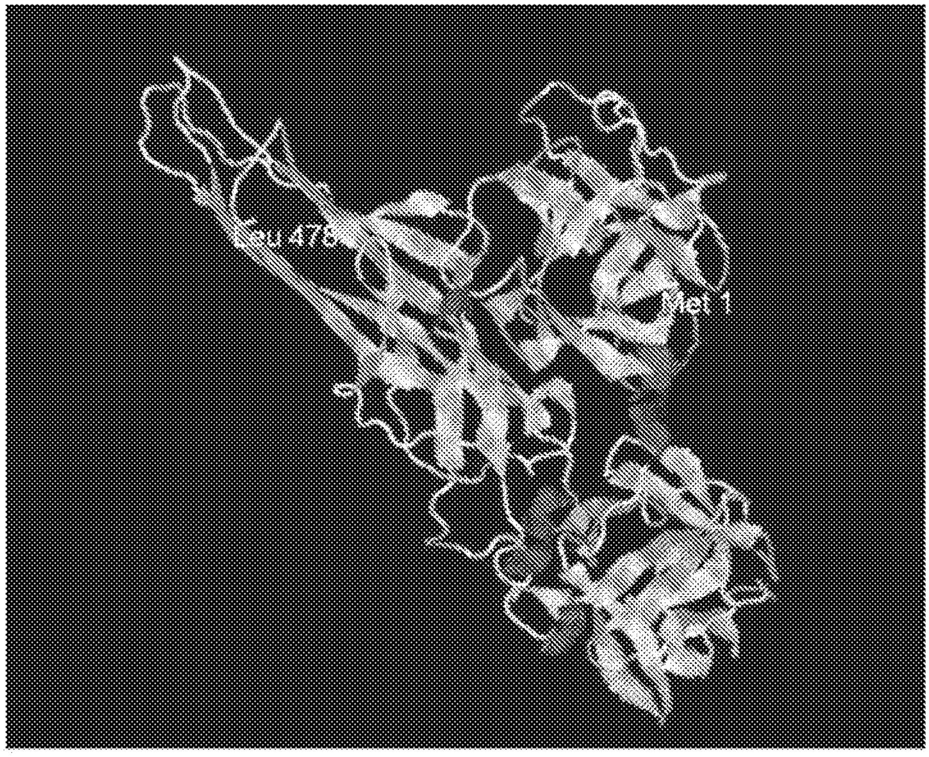
FIG. 2. Predicted protein structure of Fhb1. Dark grey ribbons represent alpha helices and light grey ribbons show beta pleated sheets, respectively. Starting and last amino acids (Methionine and Leucine) of the protein chain have been numbered.

The gene is 3,472 bp long and consists of 2 exons. The mRNA is 1,437 bp long. The transcript has 49 bp long 5' untranslated region and 216 bp long 3' untranslated regions. Exon 1 of the gene has first Agglutinin superfamily conserved domain, Exon 2 has the second Agglutinin superfamily conserved domain and ETX-MTX2 superfamily (FIG. 1). The protein is a 478amino acid long polypeptide and weighs 53.74 kilo Daltons (computationally calculated, FIG. 2). In the accompanying sequence file SEQ ID NO:1 is the Fhb1 gene sequence, SEQ ID NO:2 is the mRNA complementary (cDNA) sequence of Fhb1, SEQ ID NO:3 is the protein sequence of Fhb1.

2. Gene Expression

Expression of the gene was studied in resistant and susceptible near isogenic lines (NILs). Gene is expressed in untreated resistant plants, but is missing in susceptible near isogenic lines.

3. TILLING Based Validation of the Candidate Gene

Figure 5:
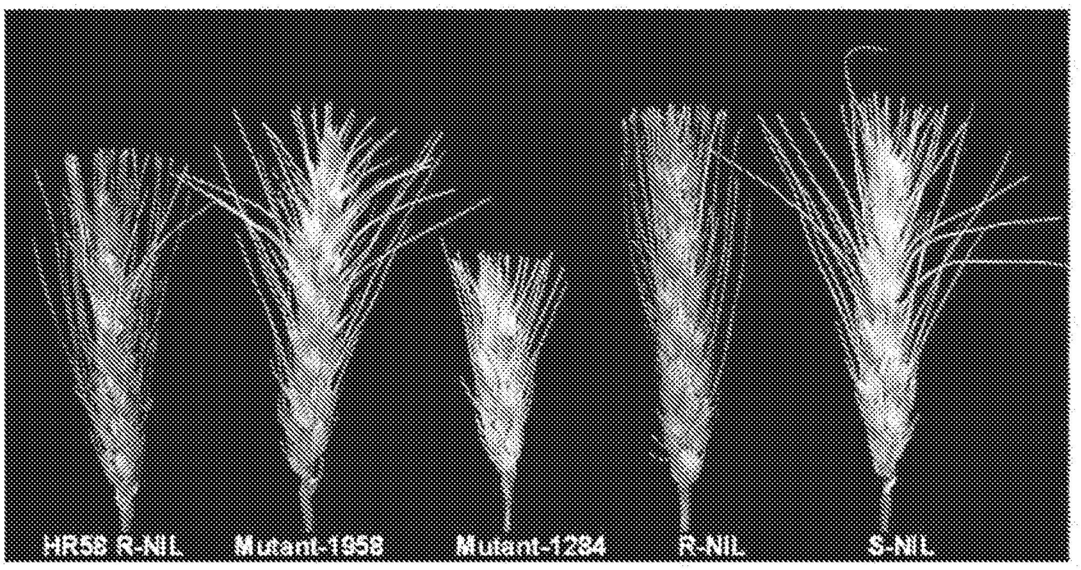
FIG. 5. Disease severity on the spikes of plants with non-sense mutations as compared with resistant and susceptible near isogenic lines (NILs) as controls. Black dots on the spikes show the point of inoculation.

For validation of the candidate gene, the powerful reverse genetics technique of TILLING was used. A total of forty mutants were identified after screening all the plants. Out of 40 mutants, fifteen were found to be silent, twelve were mis-sense, two were intronic mutations near Exon 2, and two were non-sense mutations. Nine mutants could not be sequenced successfully. Two independent mutants were identified having G>A transition, leading Tryptophan to change to stop codon at positions 233 and 361 of the protein. FIG. 3 shows the Clustal Omega alignment of the candidate gene sequences of the mutants as compared with the wild-type. FIG. 4 shows the Clustal Omega alignment of the corresponding protein of the mutants and wild type. Both the mutants were tested for their response to *F. graminearum* infection. It was found that the mutants had loss of resistance to FHB owing to the non-sense mutation in them, proving that our candidate gene is the Fhb1 gene (FIG. 5).

4. Antifungal Activity of Fhb1 Protein

Figure 6:
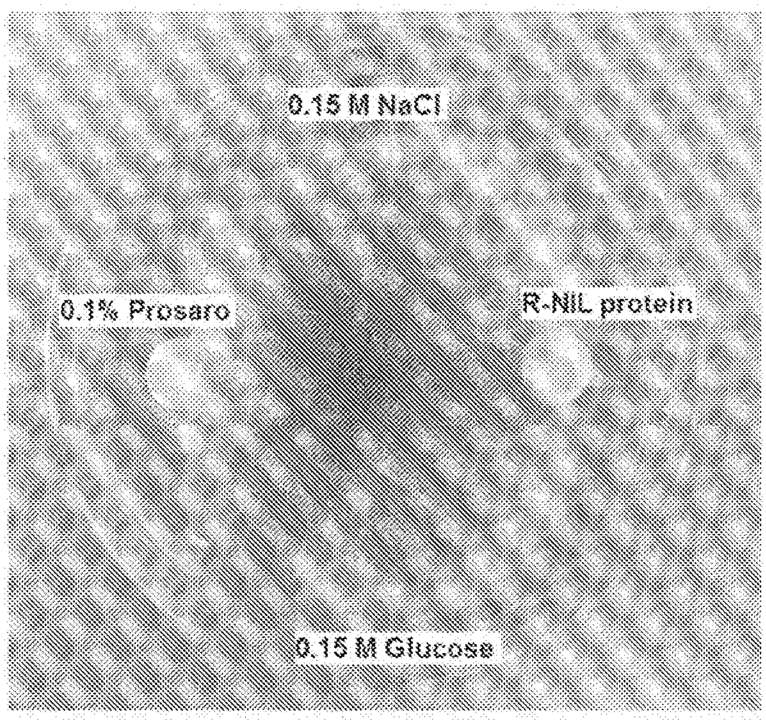
FIG. 6. Effect of the isolated protein on the spread of fungal mycelia.

Owing to the well-known affinity of lectins towards chitin, chitin columns have been used extensively to purify lectins by various workers. Antifungal activity of the isolated protein was characterized using petri-dish cultures of the fungus *F. graminearum*. Spread of the fungal mycelia was arrested on and near filter disks with the isolated protein and the fungicide Prosaro. In contrast, the mycelial growth was un-inhibited on mock and positive controls having 0.15M NaCl and 0.15M glucose, respectively, showing that the isolated protein inhibits growth of the fungus (FIG. 6).

5. Association Study of Fhb1 Gene

The haplotype of Fhb1 gene among a collection of 41 accessions known for their Fhb1 mediated resistance to FHB were determined. The Fhb1 gene was found to be present (no SNP) in all 22 of the resistant varieties tested (Sumai 3, Aso Zairai II, Nyubai, Nobeokabouzukamugi, Huangcandou, Haiyanzhong, Huoshaomai, Huang Fang Zhu, Baishanyuehuang, Abura, NobeokaBozu, Tokai 66, Shuilizhan, Sanshukomugi, Shinchunaga, Shanasui, Wangshuibai, Ning 7840, Wannin 2, WZHHS, Taiwan, 701 Chokwang). Most of the susceptible varieties had Fhb1 gene missing altogether (Chinese Spring, NTDHP, QiaomaiXiaomai, Sanyuehuang, Yangmai 4,Yangmai S,Yangmai 158, Yangmai 1, Ernie, Freedom, Wheaton, Harding, Clark, Wesley), except for 5 landraces which had a G>A transition in the intronic region 4 bp upstream of the start of Exon 2 (Nanda 2419, Funo, Emai6, Jingzhou 1, Wuhan 3). This mutation was identical to a TILLING mutant $pft^{528}$ which was also found to be susceptible to FHB. These results indicate that Fhb1 gene provides resistance to FHB.

6. Proposed Mode of Action of the Fhb1 Gene

The cloned Fhb1 gene has conserved domains, the Agglutinin superfamily domain and ETX/MTX2 superfamily domain. Agglutinin superfamily has proteins like *Amaranthus caudatus* agglutinin, which is a lectin. Although its biological function is unknown, it has a high binding specificity for the methyl-glycoside of the T-antigen, found linked to serine or threonine residues of cell surface glycoproteins. The protein is comprised of a homodimer, with each homodimer consisting of two beta-trefoil domains. Epsilon toxin (ETX) produced by *Clostridium perfringens* type B and D strains and Mosquitocidal toxin (MTX2) produced by *Bacillus sphaericus* are pore forming toxins. They attach to the plasma membranes of the host and produce toxins, leading to altered permeability and ion-efflux, causing cell death. Our hypothesis for the mode of action of the gene is that agglutinin superfamily domain of the Fhb1 protein identifies the cell surface of the fungal pathogen, and the pore-forming toxin domain kills it. Protein subcellular localization prediction software LOCTREE 3 shows that it is secreted outside cells after production, which agrees with the proposed mode of action.

The invention claimed is:

1. A method for increasing resistance to *Fusarium* head blight (FHB) infection in a plant, said method comprising:
transforming said plant with an exogenous Fhb1 nucleic acid encoding a protein to yield a transformed plant, wherein the nucleotide sequence of said exogenous nucleic acid:
(a) comprises SEQ ID NO:1, 2, 4, 5, or 6;
(b) has at least 95% sequence identity to SEQ ID NO:1, 2, 4, 5, or 6;
(c) encodes a protein comprising the amino acid sequence of SEQ ID NO: 3, 7, 8, or 9; or
(d) encodes a protein having at least 95% amino acid identity to SEQ ID NO: 3, 7, 8, or 9,
thereby increasing the resistance of said transformed plant to FHB relative to a control plant.

2. The method of claim 1, wherein said plant is a monocotyledon.

3. The method of claim 1, wherein said plant is a dicotyledon.

4. The method of claim 1, wherein said plant is selected from the group consisting of grains, legumes, and tubers.

5. The method of claim 1, wherein said plant is selected from the group consisting of wheat, oat, barley, rice, maize, millet, rye, sorghum, triticale, buckwheat, quinoa, soybeans, beans, peas, alfalfa, potatoes, sweet potatoes, cassava, and yam.

6. The method of claim 1, wherein said exogenous Fhb1 nucleic acid is stably incorporated into the transformed plant's genome.

7. The method of claim 1, wherein said transformed plant's genome comprises more than one copy of the exogenous Fhb1 nucleic acid.

8. The method of claim 1, wherein said transformed plant further comprises a second exogenous nucleic acid encoding a native resistance gene.

9. The method of claim 1, further comprising crossing said transformed plant with a second plant to produce progeny.

10. The method of claim 9, wherein said progeny comprises at least an allele of said exogenous Fhb1 nucleic acid, said progeny exhibiting at least partial resistance to FHB relative to a control plant.

11. The method of claim 9, wherein said second plant is a transgenic plant having increased resistance to FHB infection, and having an exogenous Fhb1 nucleic acid stably incorporated into its genome, wherein the nucleotide sequence of said exogenous nucleic acid:
(a) comprises SEQ ID NO:1, 2, 4, 5, or 6;
(b) has at least 95% sequence identity to SEQ ID NO:1, 2, 4, 5, or 6;
(c) encodes a protein comprising the amino acid sequence of SEQ ID NO: 3, 7, 8, or 9; or
(d) encodes a protein having at least 95% amino acid identity to SEQ ID NO: 3, 7, 8, or 9.

12. The method of claim 11, wherein said progeny is homozygous for said Fhb1 nucleic acid.

13. The method of claim 9, further comprising selecting at least one plant from said progeny that comprises said exogenous Fhb1 nucleic acid.

14. The method of claim 13, comprising detecting a marker associated with FHB-resistance in said progeny; and selecting a FHB-resistant progeny plant comprising said exogenous Fhb1 nucleic acid.

15. The method of claim 1, wherein said transforming comprises introducing into said plant a heterologous recombinant expression cassette comprising said exogenous Fhb1 nucleic acid.

16. The method of claim 15, wherein said expression cassette is introduced into said plant via particle bombardment-mediated delivery, *Agrobacterium*-mediated uptake, PEG- or electroporation-mediated uptake, viral infection, and/or microinjection.

17. A recombinant vector for conferring *Fusarium* head blight (FHB) resistance in a plant, said recombinant vector comprising an isolated Fhb1 nucleic acid operably linked to a heterologous promoter, wherein the nucleotide sequence of said nucleic acid:
(a) comprises SEQ ID NO:1, 2, 4, 5, or 6;
(b) has at least 95% sequence identity to SEQ ID NO:1, 2, 4, 5, or 6;
(c) encodes a protein comprising the amino acid sequence of SEQ ID NO: 3, 7, 8, or 9; or
(d) encodes a protein having at least 95% amino acid identity to SEQ ID NO: 3, 7, 8, or 9.

18. The recombinant vector of claim 17, wherein said heterologous promoter is a pathogen-induced promoter.

19. The recombinant vector of claim 17, wherein said heterologous promoter is a constitutively-expressed promoter.

* * * * *